(12) United States Patent
Burzell

(10) Patent No.: US 11,339,300 B2
(45) Date of Patent: May 24, 2022

(54) ANTAGONISTIC PROPERTIES OF REEF FISH MICROFLORA

(71) Applicant: Aequor, Inc., Encinitas, CA (US)

(72) Inventor: Cynthia K. Burzell, Encinitas, CA (US)

(73) Assignee: Aequor, Inc., Encinitas, CA (US)

( * ) Notice: Subject to any disclaimer, the term of this patent is extended or adjusted under 35 U.S.C. 154(b) by 236 days.

(21) Appl. No.: 16/224,429

(22) Filed: Dec. 18, 2018

(65) Prior Publication Data

US 2019/0246645 A1 Aug. 15, 2019

Related U.S. Application Data

(63) Continuation of application No. 14/305,491, filed on Jun. 16, 2014, now Pat. No. 10,188,113, which is a continuation of application No. 13/953,477, filed on Jul. 29, 2013, now abandoned, which is a continuation of application No. 13/012,312, filed on Jan. 24, 2011, now abandoned, which is a continuation of application No. 11/589,301, filed on Oct. 30, 2006, now abandoned, which is a continuation-in-part of application No. PCT/US2005/015063, filed on May 2, 2005.

(60) Provisional application No. 60/566,600, filed on Apr. 30, 2004.

(51) Int. Cl.
| | |
|---|---|
| A01N 63/20 | (2020.01) |
| C09D 5/16 | (2006.01) |
| C12N 1/20 | (2006.01) |
| C09D 5/14 | (2006.01) |
| C12R 1/01 | (2006.01) |

(52) U.S. Cl.
CPC ............ *C09D 5/1687* (2013.01); *A01N 63/20* (2020.01); *C09D 5/14* (2013.01); *C09D 5/1606* (2013.01); *C12N 1/205* (2021.05); *C12R 2001/01* (2021.05)

(58) Field of Classification Search
CPC ...... C09D 5/1687; C09D 5/14; C09D 5/1606; C12N 1/205; C12R 2001/01; A01N 63/20; A61P 31/04; A61P 31/00
See application file for complete search history.

(56) References Cited

U.S. PATENT DOCUMENTS

| | | | |
|---|---|---|---|
| 4,678,512 A | 7/1987 | Grams | |
| 4,952,419 A * | 8/1990 | De Leon | A61K 9/0024 427/2.14 |
| 5,998,200 A | 12/1999 | Bonaventura et al. | |
| 6,337,187 B1 | 1/2002 | Kapeller-Libermann | |
| 2002/0028288 A1 | 3/2002 | Rohrbaugh et al. | |
| 2002/0123077 A1 | 9/2002 | O'Toole et al. | |
| 2007/0098745 A1 | 5/2007 | Bruno | |
| 2011/0117160 A1 | 5/2011 | Bruno | |
| 2013/0315967 A1 | 11/2013 | Bruno | |

FOREIGN PATENT DOCUMENTS

WO WO2005/109960 A3 11/2005

OTHER PUBLICATIONS

Bruno et al. Biofilms 2003. ASM Conferences. 2003;1-186.*
Bruno et al., "Antagonistic Properties of Reef Fish Microflora", WINDREF Research institute Annual Report 2003; 2003; 1-51.
Henrikson et al., "A new antifouling assay method: results from field experimens using extract of four marine organisms", The Journal of Experimental Marine Biology and Ecology, 194: 157-165 (1995).
International Search Report and Written Opinion issued in PCT/US2005/015063, dated Dec. 7, 2005.
Merritt et al., "Growing and Analyzing Static Biofilms", Current Protocols in Microbiology, 1B.1.1-1B.1.17 (2005).
Torres-Vitela et al., "Incidence of Vibrio Cholerae in Fresh Fish and Ceviche in Guadalajara, Mexico", J. of Food Protection, vol. 60, No. 3, 1997, pp. 237-241.

\* cited by examiner

*Primary Examiner* — Lynn Y Fan
(74) *Attorney, Agent, or Firm* — Lee & Hayes, P.C.

(57) ABSTRACT

Disclosed herein are methods for preventing biofilm formation on a surface. The present disclosure also relates to anti-biofilm forming agents, to methods of producing and using them, and to anti-fouling coatings produced therefrom.

26 Claims, 5 Drawing Sheets

Alignment: 526 C10903 M2 con
 5.15 % 524 Psychrobacter immobilis
 5.27 % 522 Psychrobacter phenylpyruvicus
 9.32 % 526 Marinobacter hydrocarbonoclasticus
10.71 % 523 Acinetobacter baumannii
10.81 % 518 Moraxella (Moraxella) osloensis
10.84 % 526 Halomonas elongata
10.84 % 526 Halomonas pacifica
11.09 % 523 Acinetobacter genomospecies 3
11.12 % 523 Acinetobacter radioresistens
11.28 % 523 Acinetobacter haemolyticus

Neighbor Joining Tree

ANTAGONISTIC PROPERTIES OF REEF FISH MICROFLORA

CROSS REFERENCE TO RELATED APPLICATIONS

This application is a continuation of application Ser. No. 14/305,491 filed on Jun. 16, 2014, which is a continuation of application Ser. No. 13/953,477 filed on Jul. 29, 2013, which is a continuation of application Ser. No. 13/012,312 filed Jan. 24, 2011, which is a continuation of application Ser. No. 11/589,301, filed on Oct. 30, 2006, which is a continuation-in-part of International Application No. PCT/US05/015063, filed on May 2, 2005, which claims the benefit of U.S. Provisional Application No. 60/566,600 filed Apr. 30, 2004, each of which is herein incorporated by reference in its entirety for all purposes.

BACKGROUND

Microbial biofilms cause systemic infections in humans and costly marine and industrial related damage and inefficiency. They cost billions of dollars yearly in equipment damage, product contamination, energy losses and medical infections. All living and non-living marine surfaces are potential sites for microbial biofilm formation. In the human body biofilms can be associated with tissues (e.g., inner ears, teeth, gums, lungs, heart valves and the urogenital tract) and on indwelling medical devices (e.g., contact lenses, central venous catheters and needleless connectors, endotracheal tubes, intrauterine devices, mechanical heart valves, pacemakers, peritoneal dialysis catheters, prosthetic joints, tympanostomy tubes, urinary catheters, and voice prostheses). An estimated 80% of all microbial infections involve biofilms. Biofilms are a problem in the water service utilities and many industrial processes including the food, pharmaceutical, paint, oil processing and manufacturing, and engineering industries. Biofilms also cause accelerated corrosion in industrial systems, oil souring and biofouling. Biofouling of ships' hulls is a major problem for shipping worldwide.

Biofilms are extremely difficult to remove with existing technology because they can withstand high temperature (>150° C.), biocides, anti-infective compounds including antibiotics, and host immune responses. Also, the huge doses of antimicrobials required to rid systems of biofilm bacteria are environmentally undesirable and medically impractical. Thus, there is an immediate need for safe and effective products that combat biofilms.

The present inventor has discovered that bacteria isolated from the epithelial mucosal surfaces of healthy coral reef fish (e.g., *Sparisoma ninidae* and *Lutjanus purpureus*) produce signals or toxins that prevent biofilm formation. The present technology can be applied to produce anti-fouling agents, antibacterial compounds, bacteriocidal compounds, or signaling molecules which inhibit biofilm formation and/or fouling of eukaryotic organisms and are less likely to be harmful to the environment. Thus, an object of this disclosure is to protect biologic and non-biologic surfaces from biofilm formation.

SUMMARY

Reef fish have developed ways to prevent biofilm formation on their surfaces and under the skin barrier. Thus, disclosed herein is the isolation of bacteria from the surfaces of such coral reef fish (e.g., *Sparisoma ninidae* and *Lutjanus purpureus*), wherein the surfaces remain relatively free of macro-fouling. A probiotic microbial community present on the mucosal surfaces of the reef fish was found to provide broad protection against microbial settlement, infections, and macro-fouling. Further demonstrated is that the probiotic microbial community protects the fish from colonization of pathogens by producing antibacterial substances, making the environment unsuitable for foreign bacteria, or producing signaling molecules inhibiting the attachment of foreign bacteria.

Disclosed herein is the isolation of bacteria from the mucosal surface of the fish and use of their extracts to develop novel anti-biofilm forming agents. Among the many advantages of using natural compounds such as those provided herein is that they are less likely to be harmful to the body or environment. It is also advantageous to use an organism that produces an anti-biofilm signaling substance instead of an antibacterial substance. Bacteria are unable to develop resistance against a signaling molecule, thus extending the lifetime of the drug. Another advantage of using an organism that naturally has inhibitory effects on biofilm formation is that the biotechnological process to collect the substance is not likely to be hindered by genetic reversion because the wild type producer was not a result of genetic manipulation.

BRIEF DESCRIPTION OF THE TABLES

Figure 1:
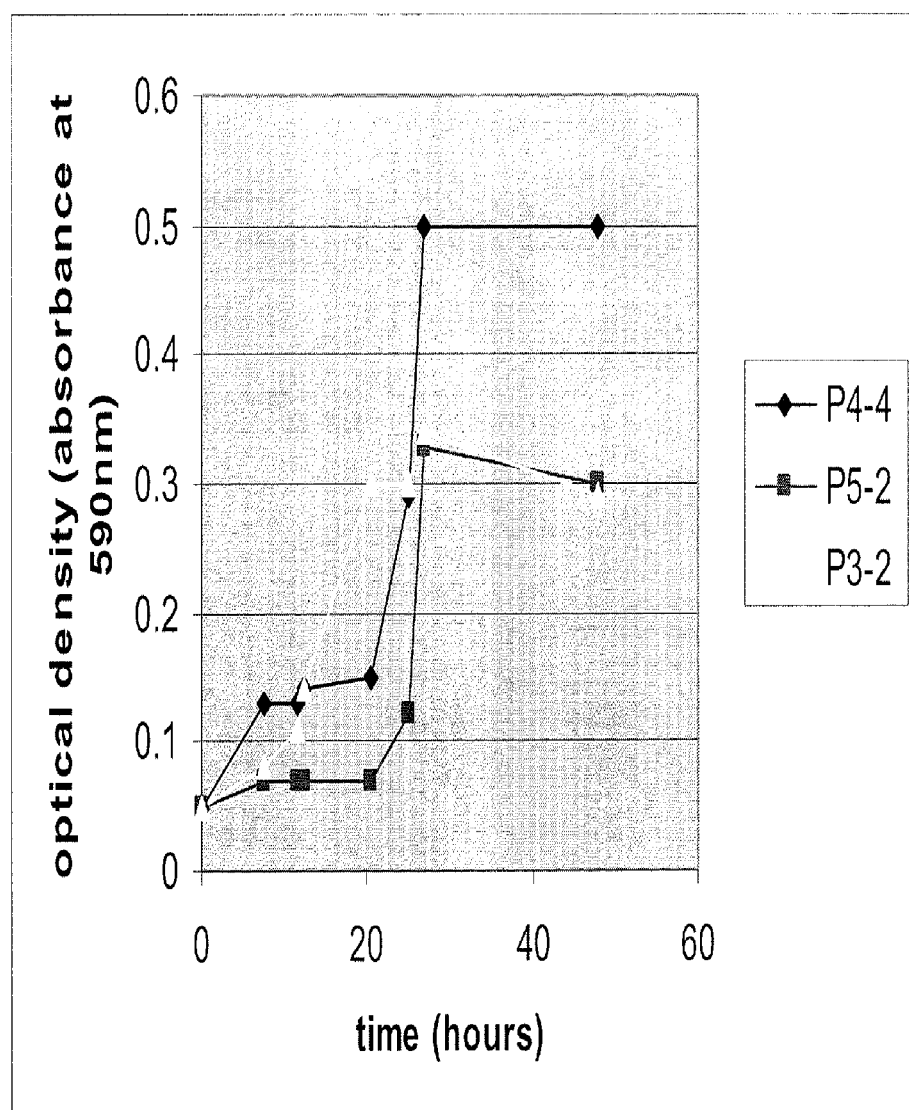
FIG. 1. This figure shows the growth curves for isolates P4-4, P5-2, and P3-2.

Table 1: Table 1 presents the culture collection catalogue of fish isolates.

Table 2: Table 2 lists the morphological characteristics of the fish skin isolates.

Table 3: Table 3 lists the physiological characteristics of the isolates from the skin of fish.

Table 4: Table 4 provides a summary of antagonistic activity of isolates against reference strains for the extract test and streak test that yielded positive results.

Table 5: Table 5 provides a summary of activity of living cells of isolates (P4-4, P5-2, P2-1, P3-2) against bacterial and eukaryotic fouling.

Table 6: Table 6 provides a summary of extract activity of isolates (P4-4, P5-2, P2-1, P3-2) against bacterial and eukaryotic fouling.

Table 7: Table 7 supplies information on the taxonomic affiliation of the isolates.

Table 8: Table 8 provides a summary of DNA GC content for isolates (P4-4, P3-2, P3-1, P5-2) and closest related species.

Table 9: Table 9 provides DNA-DNA hybridization data for isolates (P4-4, P3-2, P3-1, P5-2) and closest related species.

DETAILED DESCRIPTION

All publications and patent applications herein are incorporated by reference to the same extent as if each individual publication or patent application was specifically and individually indicated to be incorporated by reference.

The following description includes information that may be useful in understanding the present disclosure. It is not an admission that any of the information provided herein is prior art or relevant to the presently claimed inventions, or that any publication specifically or implicitly referenced is prior art.

Unless defined otherwise, all technical and scientific terms used herein have the same meaning as commonly understood by one of ordinary skill in the art to which this disclosure belongs. Although any methods and materials similar or equivalent to those described herein can be used in the practice or testing of the compositions or methods disclosed herein, the preferred methods and materials are described.

I. Definitions

As used herein, the term "biofilm" refers to a population of microorganisms (bacteria, fungi, and/or protozoa, with associated bacteriophages and other viruses) that are concentrated at an interface (usually solid/liquid) and typically surrounded by an extracellular polymeric slime matrix.

As used herein, the term "anti-fouling" refers to counteracting or preventing the building up of deposits on underwater surfaces.

As used herein, the term "anti-fouling agent" refers to compound used to protect underwater surfaces from attaching organisms.

As used herein, the term "anti-fouling coating" refers to a coating labeled and formulated for application to submerged stationary structures and their appurtenances to prevent or reduce the attachment of marine or freshwater biological organisms. Anti-fouling coatings are used to protect articles against infestation, especially ships' hulls, screens, nets, constructions, quaysides, signaling equipment and articles which come into contact with sea water or brackish water.

As used herein, the term "antimicrobial" refers to a substance that destroys or inhibits the growth of microorganisms.

As used herein, the term "biocide" refers to a chemical which can kills or inhibits the growth of living organisms such as bacteria, fungi, molds, and slimes.

As used herein, the term "biodeterioration" refers to the deterioration of materials of economic importance by microorganisms.

As used herein, the term "fouling" refers to an accumulation of marine organism deposits on a submerged surface.

As used herein, the term "hull" refers to the body or frame of a ship or boat.

As used herein, the terms "inhibit", "inhibiting" and "inhibition" refer to stopping, preventing, reducing or eliminating the growth or functioning of an organism or part of an organism. Such inhibition may adversely affect the physiological and/or morphological characteristics of a target organism.

As used herein, the term "indwelling" refers to a medical device placed or implanted within the body, such as a catheter or pacemaker.

As used herein, the term "isolate" when used as a verb refers to a process of separating a particular species, strain, or substance from a mixture, sample or biological specimen. Such a process may further involve characterizing the separated species, strain or substance.

As used herein, the term "isolate" when used as a noun refers to a particular species, strain, or substance separated from a mixture, sample or biological specimen.

As used herein, the term "medical device" refers to an instrument, apparatus, implement, machine, contrivance, implant, in vitro reagent, or other similar or related article, including any component, part or accessory, which is intended for use in the diagnosis of disease or other conditions, or in the cure, mitigation, treatment, or prevention of disease, in man or other animals, or intended to affect the structure or any function of the body and which does not achieve its primary intended purposes through chemical action and which is not dependent upon being metabolized for the achievement of its primary intended purposes.

As used herein, the term "target organism" refers to any organism for which inhibition is desired. Such organisms include but are not limited to bacteria, photosynthetic eukaryotic organisms, and non-photosynthetic eukaryotic organisms.

II. Fish Microflora

The marine environment is a great potential reservoir for novel therapeutics. Marine eukaryotes have developed natural means for preventing colonization of bacteria and higher organisms. They developed two strategies to protect against biofouling: the secretion of signaling compounds and housing of probionts. Both strategies interfere with signals regulating biofilm formation. Fish possess bacterial populations on or in their skin, gills, digestive tract, and light-emitting organs. In addition, the internal organs (kidney, liver, and spleen) of healthy fish may contain bacteria, but there is debate on whether or not muscle is actually sterile. The numbers and taxonomic composition of the bacterial populations often reflect those of the surrounding water. The role of the bacteria includes the ability to degrade complex molecules (therefore exercising a potential benefit in nutrition), to produce vitamins and polymers, and to be responsible for the emission of light by the light-emitting organs of deep-sea fish.

Few studies have been done on indigenous fish surface microflora of healthy fish. The surface of fish consists of skin, scale and mucus. The microorganisms that inhabit the slime and external surfaces of healthy marine fish include, *Pseudomonas, Vibrio, Achromobacter, Flavobacterium/Cytophaga, Moraxella, Micrococcus, Acinetobacter, Photobacterium, Bacillus*, and *Aeromonas*. Bacteria may assist the fish in locomotion and protection against pathogens.

Bacteria associated with a fast moving cornetfish (*Fistularia commersonii*) were hydrophobic and produced drag-reducing slime, which allow for the fish to travel faster in the water. One hundred forty five bacteria were isolated from the skin of rainbow trout (*Oncorhynchus mykiss*). The majority of these were non-fermentive Gram-negative rods (*Pseudomonas* and *Acinetobacter/Moraxella*) and three had antagonistic properties toward fish pathogenic bacteria.

The bacteria may be selected for by the fish if they are beneficial for the fish. Bacteria isolated from the skin of a healthy turbot (*Scophthalmus maximus*) differed from the flora in the surrounding water. The microorganisms may be selected for because of the specific sugars in the fish mucus. The colonization of bacteria begins with a chemotactic attraction of the bacteria to the mucus, followed by penetration and adhesion to receptors in the mucus or epithelial cells. In contrast, fish mucus can have inhibitory effects on bacteria. The inhibition can be caused by immunoglobulins, lysozyme, and continuous shedding.

III. Microbial Biofilms

A biofilm is an assemblage of surface-associated microbial cells that is enclosed in an extracellular polymeric substance matrix. Biofilms may form on a wide variety of surfaces, including living tissues, indwelling medical devices, industrial or potable water system piping, or natural aquatic systems.

Biofilms are composed primarily of microbial cells and Extracellular Polymeric Substances (EPS). Noncellular materials such as mineral crystals, corrosion particles, clay or silt particles, or blood components, depending on the environment in which the biofilm has developed, may also be found in the biofilm matrix. EPS may account for 50%, 60%, 70%, 80%, and even up to 90% of the total organic carbon of biofilms and can be considered the primary matrix material of the biofilm. EPS may vary in chemical and physical properties, but it is primarily composed of polysaccharides. Different organisms produce differing amounts of EPS and that the amount of EPS increases with age of the biofilm. EPS is highly hydrated because it can incorporate large amounts of water into its structure by hydrogen bonding and prevents desiccation in some natural biofilms. EPS may associate with metal ions, divalent cations, other macromolecules (such as proteins, DNA, lipids, and even humic substances). EPS production is known to be affected by nutrient status of the growth medium; excess available carbon and limitation of nitrogen, potassium, or phosphate promote EPS synthesis. Slow bacterial growth will also enhance EPS production. EPS may also contribute to the antimicrobial resistance properties of biofilms by impeding the mass transport of antimicrobials through the biofilm, probably by binding directly to these agents.

The development of a biofilm occurs in distinct stages. Once a conditioning film develops on the surface, planktonic bacteria attach to the surface, proliferate, excrete EPS, communicate, and build complex structures. The structures are composed of single-species and multi-species bacterial microcolonies that take the form of towers, mushroom shapes, and streamers with water channels running through them. Proximity of cells within the microcolony (or between microcolonies) provides an ideal environment for creation of nutrient gradients, exchange of genes, and quorum sensing. Since microcolonies may be composed of multiple species, the cycling of various nutrients (e.g., nitrogen, sulfur, and carbon) through redox reactions can readily occur in aquatic and soil biofilms. Organisms composing the biofilm may also have a marked effect on the biofilm structure. Number of component organisms may affect the thickness of the biofilm. Structure may also be influenced by the interaction of particles of non-microbial components from the host or environment.

The bacteria in the biofilm are phenotypically different than their planktonic form, showing a decrease in growth rate and different gene expression. Bacteria in a biofilm are protected from grazing and secondary environmental stresses such as, ultraviolet (UV) exposure, desiccation, and temperature shifts. More nutrients are made available to bacteria in a biofilm, however, diffusion of nutrients slows considerably deep in the biofilm.

Signaling molecules are produced when the cells reach a critical density and the biofilm is formed. For example, signals are used for bacterial communication and formation of the microcolony architecture or cell detachment from biofilms. Biofilm cells may be dispersed either by shedding of daughter cells from actively growing cells, detachment as a result of nutrient levels or quorum sensing, or shearing of biofilm aggregates (continuous removal of small portions of the biofilm) because of flow effects. The pattern and development of a biofilm, however, is not only regulated by QS. Different conditions such as shear flow of the fluid and nutrient concentrations affect the biofilm phenotype and physiology of bacteria. Biofilms also provide an ideal niche for the exchange of extrachromosomal DNA (plasmids). Conjugation (the mechanism of plasmid transfer) occurs at a greater rate between cells in biofilms than between planktonic cells.

IV. Pathogenic Infections Associated with Biofilms

Biofilms develop preferentially on inert surfaces, or on dead tissue, and occur commonly on medical devices and fragments of dead tissue such as sequestra of dead bone; they can also form on living tissues, as in the case of endocarditis. Characteristics of biofilms involved in infectious disease processes include a) detachment of cells or biofilm aggregates may result in bloodstream or urinary tract infections or in the production of emboli, b) cells may exchange resistance plasmids within biofilms, c) cells in biofilms have dramatically reduced susceptibility to antimicrobial agents, d) biofilm-associated gram-negative bacteria may produce endotoxins, and e) biofilms are resistant to host immune system clearance.

Formation of these sessile communities and their inherent resistance to antimicrobial agents are at the root of many persistent and chronic bacterial infections. The Center for Disease Control and Prevention (CDC) estimated that 65% of all chronic infections can be attributed to microbial biofilms.

In the human body biofilms are associated with tissues and on indwelling medical devices. Tissue associated infections include native valve endocarditis (NVE), otitis media (OM), chronic bacterial prostatitis, cystic fibrosis (CF), and periodontitis. Biofilms on indwelling medical devices can occur on central venus catheters, urinary catheters, prosthetic heart valves, contact lenses, and intrauterine devices (IUDs). Medical devices such as dental unit equipment and waterlines can be a source of infections.

NVE is caused by the interaction between the vascular endothelium and bacteria or fungi in the bloodstream. The microorganisms involved include Streptococci sp., Staphylococci sp., *Candida*, and *Aspergillus* sp. OM is a disease of the middle ear with an inflamed mucoperiosteal lining. The microorganisms involved include *Streptococcus pneumoniae, Haemophilus influenzae, Moraxella catarrhalis, Staphylococcus aureus, Staphylococcus epidermidis*, and *Pseudomonas aeruginosa*. Chronic bacterial prostatitis is a bacterial infection of the prostate gland by *Escherichia coli, Klebsiella* sp., *Proteus* sp., *Serratia* sp., *P. aeruginosa*, and *Enterococcus faecalis, Bacteroides* sp., *Gardnerella* sp., and *Corynebacterium* sp. CF is a chronic lethal single gene disorder with symptomatic infection of the lower respiratory system by *P. aeruginosa, S. aureus* and *Burkholderia cepacia*. Periodontal diseases are infections of the supporting tissues of teeth that range from mild to chronic. The bacteria involved include, *Actinomyces naeslundii, Bacteroides forsythus, B. intermedius, B. pneumosintes, Eubacterium brachy, E. timidum, Fusobacterium nucleatum, Haemophilus aphrophilus, Lactobacillus* spp., *Peptostreptococcus micros, Porphyromonas gingivalis, Pseudomonas anaerobius, Selenomonas sputigena*, and *Woline/la recta*.

Many common bacterial pathogens exist in animals as biofilms. Typical animal diseases where bacterial biofilms are believed to be involved based on histopathologic and ultrastructural appearance of the bacteria within tissue include: mastitis (*Streptococcus agalactiae, S. aureus*), pneumonia (*Mannheimia haemolytica, Pasteurella mu/tock/a*), liver abscess (*Fusobacterium necrophorum*), lymphadenitis (*Corynebacterium pseudotuberculosis, Streptococcus* spp.), enteritis (*E. coli, Salmonella* spp.) and wound infections (*S. aureus, P. aeruginosa*).

V. Indwelling Medical Device Associated Infections

A spectrum of indwelling medical devices (e.g., ocular lenses, dental implants, central venous catheters and needleless connectors, endotracheal tubes, intrauterine devices, mechanical heart valves, coronary stents, vascular bypass grafts, pacemakers, peritoneal dialysis catheters, prosthetic joints, central nervous system shunts, tympanostomy tubes, urinary catheters, and voice prostheses) or other devices used in the health-care environment have been shown to harbor biofilms, resulting in measurable rates of device-associated infections.

Biofilms on indwelling medical devices may be composed of gram-positive or gram-negative bacteria or yeast. Bacteria commonly isolated from these devices include the gram-positive *E. faecalis, S. aureus, S. epidermidis,* and *Streptococcus viridans*; and the gram-negative *E. coli, Klebsiella pneumoniae, Proteus mirabilis,* and *P. aeruginosa*. Biofilms may be composed of a single species or multiple species, depending on the device and its duration of use in the patient.

Device-related infection results from the introduction of organisms, primarily bacteria, during the device insertion or implantation procedure, or from attachment of bloodborne organisms to the newly inserted device and their subsequent propagation on its surface. The organisms first attach to the device surface through the secretion of polymers (polysaccharides) or the extension of fibrils, which anchor the bacteria to the surface. After attachment, cell division of the bacteria produces sister cells that form microcolonies and create a protective barrier commonly known as biofilm or bioslime. Once this barrier is formed, the bacteria can propagate within the biofilm and release substantial amounts of bacterial cells into the surrounding fluids and tissues. The infections that ensue can be difficult to treat, because the body's macrophages and antibiotics are unable to reach the primary source of the infecting bacteria. Often, effective treatment requires removal of the offending device.

Central venous catheter infections pose the greatest risk of the indwelling medical devices infections, the organisms involved include *S. aureus, S. epidermidis, P. aeruginosa, K. pneumoniae, E. faecalis,* and *Candida albicans*. Urinary catheter infections can be caused by *Acinetobacter calcoaceticus, Enterobacter aerogenes, E. coli, E. faecalis, K. pneumoniae, M. morganii, P. aeruginosa, P. mirabilis, Providencia stuartii, Proteus vulgaris,* and *S. epidermidis*. The organisms that may colonize prosthetic heart valves include, but are not limited to, Streptococci sp., *S. aureus,* gram-negative coccobacilli, or fungi. Organisms that can attach to contact lenses include *P. aeruginosa, S. aureus, S. epidermidis, Serratia* sp., *E. coli, Proteus* sp., and *Candida* sp. IUDs can be contaminated with *S. epidermidis, Enterococcus* sp. *Lactobacillus plantarum, Corynebacterium* sp., *Micrococcus* sp., *C. albicans*, and *S. aureus*.

The anti-biofilm substances produced by the isolates disclosed herein can be used on the surface of or within these devices to provide long term protection against bacterial colonization and reduce the incidence of device-related infections. These substances can also be incorporated as an anti-biofilm forming agent, in combination with an antibiotic, into coatings for indwelling medical devices. Coatings will sufficiently kill or inhibit the initial colonizing bacteria and prevent device-related infection as long as the substance is presented in an inhibitory concentration at the device-microbe interface.

The medical devices which are amenable to coatings of the subject anti-biofilm substances generally have surfaces composed of thermoplastic or polymeric materials such as polyethylene, Dacron, nylon, polyesters, polytetrafluoroethylene, polyurethane, latex, silicone elastomers and the like. Devices with metallic surfaces are also amenable to coatings with the anti-biofilm substances. Such devices, for example bone and joint prosthesis, can be coated by cement mixture containing the subject anti-biofilm substances. During implant use, the anti-biofilm substances leach from the cement into the surrounding prosthesis surface environment.

Various methods can be employed to coat the surfaces of medical devices with the anti-biofilm substances. For example, one of the simplest methods would be to flush the surfaces of the device with a solution of the anti-biofilm substance. The flushing solution would normally be composed of sterile water or sterile normal saline solutions. Another method of coating the devices would be to first apply or adsorb to the surface of the medical device a layer of tridodecylmethyl ammonium chloride (TDMAC) surfactant followed by a coating layer of anti-biofilm substance. For example, a medical device having a polymeric surface, such as polyethylene, silastic elastomers, polytetrafluoroethylene or Darcon, can be soaked in a 5% by weight solution of TDMAC for 30 minutes at room temperature, air dried, and rinsed in water to remove excess TDMAC. Alternatively, TDMAC precoated catheters are commercially available; for example, arterial catheters coated with TDMAC are available from Cook Critical Care (Bloomington, Ind.). The device carrying the absorbed TDMAC surfactant coated can then be incubated in a solution of the anti-biofilm substance for one hour, washed in sterile water to remove unbound anti-biofilm substance and stored in a sterile package until ready for implantation. A further method useful to coat the surface of medical devices with the subject antibiotic combinations involves first coating the selected surfaces with benzalkonium chloride followed by ionic bonding of the anti-biofilm substance composition. See, e.g., Solomon, D. D. and Sherertz, R J, J. Controlled Release 6:343-352 (1987) and U.S. Pat. No. 4,442,133. Alternative methods and reagents provided in U.S. Pat. Nos. 4,107,121, 4,442,133, 4,678,660 and 4,749,585, 4,895,566, 4,917,686, 4,952,419, and 5,013,30, can be used to coat devices with the anti-biofilm substances.

The anti-biofilm agent can be directly incorporated into the polymeric matrix of the medical device at the polymer synthesis stage or at the device manufacture stage. The anti-biofilm agent can also be covalently attached to the medical device polymer. These and many other methods of coating medical devices appear in numerous patents and medical journal articles. As is evident, one of ordinary skill having benefit of this disclosure would be apprised of several different methods of coating various medical device surfaces with the subject inventive anti-biofilm coatings.

VI. Resistance to Host Immune Responses and Antimicrobial Agents

Infections that involve a biofilm mode of growth are generally chronic and are often difficult to treat. Biofilms grow slowly, in one or more locations, and biofilm infections are often slow to produce overt symptoms. Bacteria living in biofilms can withstand host immune responses, and they are much less susceptible to antibiotics than their nonattached individual planktonic counterparts. This protection can be attributed to five phenomena that occur when bacteria are living in a biofilm. First is the concept that bacteria living in close proximity to each other exchange plasmids efficiently. Thus, if antibodies are developed, the resistant bacteria are selected for, and an antibody-resistance biofilm will result. The second premise is that white blood cells (WBC), antibodies, and antibiotics are unable to penetrate the biofilm EPS matrix well. The third deals with the physiological change of the bacteria. A change in phenotype can allow for the bacteria to enhance their activity against the immune response even if WBC and antibiotics can penetrate. The fourth phenomenon is that some bacteria deep in the biofilm have a reduced growth rate which makes them more resistant to certain agents. Lastly, bacteria in biofilms may avoid the immune responses by mimicking human tissue with EPS material. For these reasons biofilm infections typically show recurring symptoms, after cycles of antibiotic therapy, until the sessile population is surgically removed from the body.

VII. Industrial Biofilm Damage

Biofilms in industrial systems cause severe clogging, contamination, and biodeterioration. Bacterial contamination of the water distribution systems can occur if biofilms are sloughed off naturally or removed by treatment. Biofilms in drinking water piping systems accommodate *Heliobacter pylori*, *Mycobacterium* spp., and protozoa infected with *Legionella pneumophila*. This results in decreased water quality and increased treatment costs and health risks. Biofilms in pipes carrying water or other liquids cause reduced flow and increased resistance to flow. Formation of biofilms on probes, sensors, screens and filters results in reduced efficiency. Microbial films that grow on the walls of heat exchanger tubes create additional heat transfer and fluid flow resistances. Formation of biofilms on ship hulls leads to biofouling resulting in increased fuel consumption and cleaning costs. The food industry is also affected by the contamination caused by these films which adhere easily to the walls of food processing equipment. Biofilms in cooling towers results in reduced performance, degradation of material and also provides a reservoir for pathogens. Building materials such as stone, bricks and concrete or clay based roof tiles, mortars and especially all new materials for insulation and damming of humidity often contain organic compounds and are very susceptible to growth of sub-aerial biofilms creating an anaesthetic biopatina and reducing durability. Chemical and physical biodeteriorative forces, phenomena and processes further create damage on old and new buildings. Depending on the environmental conditions water retention and penetration the surface biofilms may transform into networks going deeper into the material. Biocide impregnation of new materials and biocide treatments of monuments create health and environmental hazards.

Microbial induced corrosion (MIC) is the deterioration of materials caused by microorganisms under anaerobic or aerobic conditions. MIC is associated with localized, under-deposited, pitting corrosion, and accounts for 15 percent to 30 percent of the corrosion-related pipeline failures in the gas and nuclear industries alone. It is also a major cause of failures in the water treatment and chemical industries, and is also associated with corrosion failures, blockage and souring in gas and oil production and storage. To prevent MIC many chemicals are used commercially, but few of them have been tested extensively before they were released. Hexavalent chromium (Cr VI) was used as a component of anti-corrosive coatings (chrome plating and spray coatings). The Occupational Safety and Health Administration (OSHA) recognizes that Cr VI is a hazardous potential lung carcinogen, it can cause permanent eye damage, and it can cause skin and nasal ulcers.

VIII. Quorum Sensing Signaling Molecules

Biofilm formation and other multicellular-like activities that cover a wide range of processes such as, swarming, bioluminescence, virulence, and dispersal are a result of bacterial communication, referred to as quorum sensing (QS). Numerous bacteria communicate intercellularly, to regulate the transcription of multiple target genes in concert with their cell density, through the production of one or more diffusible signal molecules. In the case of biofilm formation, bacteria multiply, reach a critical number of cells, and then produce signaling molecules (autoinducers). The process of detachment of bacteria from the biofilm occurs when some cells in the interior of a cluster use QS to revert to their planktonic form, an opening is created and the planktonic cells are allowed to disperse. Dispersal is thought to occur naturally when conditions change favoring the planktonic form and/or cell clusters reach a size greater than 40 µm×10 µm.

There are two types of QS systems. The LuxI/LuxR QS system used by Gram-negative bacteria produces acylated homoserine lactones (AHLs) and quinolones that freely diffuse in and out of each cell. Thus, the AHL concentration is proportional to cell density. Once a threshold of AHL concentration is achieved, the autoinducer interacts with the LuxR protein that binds DNA promoter elements and activates the transcription and expression of QS related genes. Over 70 species of Gram-negative bacteria use LuxI/LuxR quorum-sensing systems, including the genera *Agrobacterium, Aeromonas, Burkholderia, Chromobacterium, Citrobacter, Enterobacter, Erwinia, Hafnia, Nitrosomonas, Obesumbacterium, Pantoea, Pseudomonas, Rahnella, Ralstonia, Rhodobacter, Rhizobium, Serratia, Vibrio, Xenorhabdus*, and *Yersinia*.

Gram-positive bacteria use an oligopeptide/two-component QS system. The signaling molecules involved are autoinducing peptides and lactones (butyrolactone). AIPs typically consist of 5-17 amino acids. ATP-binding cassette (ABC) transporters usually process the precursor peptides and export them as autoinducers. This QS system differs from the LuxI/LuxR system used by Gram-negative bacteria because cell-surface oligopeptide transporters are needed to secrete AIP into the environment because the Gram-positive bacterial cell membrane is not permeable to AIPs. Once the signals reach a critical level they are recognized by sensor kinase proteins on a histidine residue and this phosphorylates an aspartate residue which activates/represses the transcription of the target gene. Bacteria that produce AIPs include *S. aureus, S. epidermidis, Streptococcus gordonii, Streptococcus pyogenes, Streptococcus pneumoniae*.

Some Gram-negative bacteria *Vibrio harveyi, V. cholerae, E. coli*, and *Salmonella typhimurium* and Gram-positive bacteria *S. aureus, S. pyogenes, S. pneumoniae, Bacillus subtilis*, and *Clostridium perfringens* can also produce universal autoinducing compounds (AI-2s). The AI-2 system was first observed with the Gram-negative bioluminescent shrimp pathogen *V. harveyi*, which used an intraspecies signaling molecule and an interspecies autoinducer to regulate light production. AI-2 signaling has been adapted by the different bacteria that use it to influence virulence, biofilm formation, and a variety of niche-specific behaviors. AI-2 signaling is involved with virulence factors in *S. pyogenes* and *V. harveyi*, and *S. aureus*. AI-2 is involved in the mixed-species biofilm formation between two oral bacteria, *Streptococcus gordonii* and *Porphyromonas gingivalis* as well as *S. aureus*. AI-2 is also associated with tight adherence to intestinal epithelia by *E. coli*.

IX. Antimicrobials

Antimicrobial classification can be based on bacterial spectrum (broad versus narrow), route of administration (injectable versus oral versus topical), type of activity (bactericidal versus bacteriostatic), or chemical structure. Antibiotics are produced by microorganisms and have antagonistic effects on other microorganisms. They target metabolism, cell wall synthesis, protein synthesis, nucleic acid synthesis, cell membrane permeability or transport. These include bacteriostatic drugs that inhibit growth or bacteriocidal drugs that kill the microorganism. Bacteriocins are substances produced by bacteria that kill closely-related species without rupturing cell walls and membranes. The aim of antimicrobial chemotherapy is to harm the microorganism but not be toxic to the host.

Antimetabolites are structural analogs of normal metabolites that inhibit the action of specific enzymes. Cell wall synthesis inhibitors may inhibit trans-peptidation, inhibit the synthesis of peptidoglycan, act in the cytoplasm, in the membrane, or in the cell wall. Cell wall synthesis inhibitors include 13-lactam drugs: penicillins, cephalosporins, carbapenems. Penicillins inhibit the trans-peptidation enzymes involved in peptidoglycan synthesis for Gram-positive and Gram-negative bacteria. Cephalosporins and Carbapenems have mechanisms of action similar to penicillin. The cephalosporin antibiotics was isolated from a fungus of the Cephalosporilum genus, that inhibited Gram-positive and Gram-negative bacteria, isolated from
seawater near a sewage outlet in Cagliari, Sardinia, Italy. Protein synthesis inhibitors are known as broad-spectrum antibiotics that require bacterial growth to be effective. Protein synthesis inhibitors include aminoglycosides, macrolides, lincomycins, tetracyclines, chloramphenicol, and griseofulvin. Aminoglycosides are bacteriocidal for Gram-negative bacteria and bind to the 30S ribosomal subunit and they may irreversibly block translation initiation and/or cause mRNA misreading. Bacteriostatic macroglides and lincomycins bind to the 23S RNA in the 50S ribosomal subunit and block translation. Tetracylines are bacteriostatic and bind to the ribosomal subunit preventing aminoacyl tRNA from binding the acceptor site. Chloramphenicol binds to the SOS ribosomal subunit and inhibits peptide-bond formation thus making it bacteriostatic for Gram-positive and Gram-negative bacteria. Griseofulvin is a fungistatic drug that inhibits protein assembly and is active against fungi with chitin in the cell walls. Nucleic acid synthesis inhibitors inhibit DNA or RNA synthesis. Ethambutol inhibits mycobacterial mycolic acid biosynthesis. Cytoplasmic membrane inhibitors alter plasma membrane osmotic properties or lipid synthesis in the fungal membrane.

Bacteriocins are proteinaceous toxins produced by bacteria that inhibit the growth of a narrow range of bacteria. Bacteriocins include lactic acid produced by lactiobacilli are part of the intestinal floral of healthy fish, mutacins produced by *Streptococcus mutans* an indigenous oral bacteria, and colicins produced by *E. coli* and other members of Enterobacteriaceae. Bacteriocins may inhibit the growth of pathogens in the surrounding environment.

Anti-viral compounds inhibit viral replication. These compounds target viral nucleic acid replication, host-cell receptor recognition, the penetration and uncoating process, or specific enzyme functions. The agents are inhibitors of herpesviruses, retroviruses, or other viruses including influenza virus.

The bacterial isolates and their extracts can be used as antibacterial or bactericidal agents to remove disease-causing organisms from external surfaces. They can be used in different products such as soaps, detergents, health and skincare products and household cleaners. The antibacterial agents can be used alone, or in combination with other antimicrobial agents.

X. Fouling

Fouling is an undesirable growth of biological material on a surface immersed in water. Fouling usually starts with adhering and spreading of populations of bacteria over faces that are in contact with water. The bacteria pioneers are followed by numerous different algae, invertebrate larvae, hydroids, bryozoans, sponges, tunicates, echinoderms, cnidarians, and coelenterates.

There are many advantages for marine foulers to be attached to a surface on biofilms. The most important advantage deals with supplying the foulers with nutrients that are otherwise limited due to the capacity of the microorganism to scavenge microelements from the water. Iron, phosphorous, and reduced nitrogen are elements concentrated in biofilms that fouling organisms can utilize. Other benefits of attachment to a surface deal with the physical attachment itself, exposure, and protection. Stable settlement is beneficial to filter feeding organisms because it allows them to extract nutrients from the water passing by. Algae and invertebrate larva depend on attachment for their growth and metamorphosis. Photosynthesizing organisms, if attached in the photic zone, can benefit from exposure to sunlight. The ability to attach guarantees distribution to new energy-rich environments as well as protection against predation. These benefits provide a selective advantage to the fouling organisms.

However, fouling creates many problems. Fouling results in increased drag, weight and corrosion for marine structures; decreased aesthetic appearance of the marine structure; and increased maintenance costs associated with removal of the fouling and repair of the structure. Settlement of the foulers on the hulls of boats creates an increase in drag. Just a small amount of fouling can lead to an increase of fuel consumption of up to 40%, and possibly as much as 50%, since the resistance to movement will be increased. Vessel bottoms not protected by anti-fouling systems may gather 150 kg of fouling per square meter in less than six months of being at sea. On a very large crude carrier with 40,000 square meters of underwater area, this would add up to 6,000 tons of fouling. The cost related to fouling is estimated at 6 billion USO for 2002.

Related to boat fouling is the introduction of invasive marine species brought by the boats to new environments lacking predation of the intruding species. Invasive species can disrupt a delicate ecosystem by decreasing dissolved oxygen in the water, altering light levels, changing the soil chemistry, and increasing surface run off and erosion. This can displace native species, lead to extinction, and cause problems for local economies.

Marine fouling occurs not only on marine vessels such as ship's hulls and drive systems, but also on other structures exposed to sea water. Such structures may include: pilings, marine markers, undersea conveyances like cabling and pipes, fishing nets, bulkheads, cooling towers, and any device or structure that operates submerged.

The effect of fouling on some marine organisms can be detrimental and sometimes fatal. The epibiont growth of the freshwater sponge (*Porifera* sp.) on adult zebra mussel (*Dreissena polymorpha*) negatively impacts the growth survivability of the zebra mussel. The sponge caused reduction of glycogen, tissue loss, and mortality. When the fouler is a parasite to the host, it is beneficial to the host to have protection against fouling.

XI. Anti-Fouling Strategies by Plants and Animals

In the marine environment all surfaces are subjected to fouling. Plants and animals have developed strategies to protect themselves against detrimental biofilm formation and fouling including, the possession of spines, surface sloughing, production of mucus, the secretion of secondary metabolites (signals or toxins) and the housing of probionts. These strategies are employed effectively by a variety of organisms.

Plants have been shown to produce compounds that reduced biofilms by 65-75%. Algae secrete anti-fouling substances on their surfaces. Cross-kingdom signaling molecules, brominated furanones, produced by the red algae, *Delisea pulchra*, is a molecular analog of AHLs that prevented biofilm formation, reduce the settlement of barnacles, and control the development of the fertilized eggs of the fouling alga *Ulva*. Changing a hydroxyl group to an acetate group on the furanone increased the anti-fouling activity by orders of magnitude. The eelgrass, *Zostra marina*, produced zosteric acid, a sodium salt of a sulfated phenolic acid, that is an anti-fouling agent against barnacles and tubeworms. The sulphate ester group on zosteric acid may be responsible for the anti-fouling activity.

Octocorals (*Dendronephthya* sp. and *Sinularia* sp.) produced anti-fouling trigonelline and diterpenoid lipids. The whip coral, *Leptogorgia virgulata*, produced two anti-fouling lipids, pukalide and epoypukalide against barnacles. A sea pansy, *Renilla reniformis*, produced a group of anti-fouling diterpene compound called renillafoulins. For the pukalide and renillafoulin molecules, the anti-fouling activity is attributed to small oxygen containing rings known as lactones and furans.

The bryozoan, *Zoobotryon pellucidum*, produced toxic tribromogramine that inhibits larvae settlement. The sponge, *Mycale microsigmatosa* and the gorgonian, *Phyllogorgia dilate* prevented the attachment of barnacles in situ. The sponge, *Protophlitaspongia aga*, produced a pyrimidine derivative, 3,4,5,6-tetrahydro-6-hydroxymethyl-3,6-dimethyl-4-pyrimidinecarboxylic acid and zooanemonin that are active against the barnacle, *Ba/anus amphitrite* and α-nicotinamide ribose that inhibited germination and attachment of *Ulva* spores. The sponge, *Acanthella cavernosa* and three species of nudibranchs of the family Phyllidiidae produced sesquiterpenes and diterpenes that were active against cyrid larvae of the barnacle *Ba/anus amphitrite*. Terrestrial plants and fruits have also developed means for protecting themselves against bacterial and fungal colonization. Garlic produced small peptides that affected 74 QS regulated genes for biofilm formation in *Pseudomonas aeruginosa* (PA01).

The housing of probionts is another way plants and animals are able to prevent the colonization of common fouling organisms such as, algal spores, bacteria, invertebrate larvae, and fungi. Signaling molecules produced by bacteria can inhibit the attachment of the target fouling organisms providing protection for the host. Bacteria isolated from rock surfaces, marine animals, and marine algae inhibited vertebrate larva by 10%, 30%, and 74% respectively. Significant reduction of fouling has been inhibited by bacteria isolated from the green algae, *Ulva lactuca* and the tunicate, *Giana intestinalis*. Five epiphytes of the common green alga, *U. lactuca*, prevented the settlement of invertebrate larvae and germination of algal spores. Three of the isolates also inhibited the growth of a variety of bacteria and fungi. Phylogenetic positions, determined by 16S ribosomal subunit DNA sequencing, showed a close affiliation for these bacteria with the genus *Pseudoalteromonas* and, in particular, with the species *Pseudoalteromonas tunicata*. *P. tunicata*, a dark green pigmented marine bacterium, isolated from *C. intestinalis*, produced a compound inhibitory against the largest range of organisms, including various bacteria (including *Bacillus subtilis*), green algal spores (*U. lactuca*), red algal spores (*Polysiphonia* sp.), sea squirt larvae (*C. intestinalis*), barnacle larvae (*Ba/anus amphitrite*, tube worm larvae (*Hydroides elegans*), fungi (*Penicillium digitatum*) and yeast (*Saccharomyces cerevisiae*).

Different colored mutants were used to determine that there is a correlation between yellow pigment component of the green colored *P. tunicata* with the anti-fouling properties. *P. tunicata* is a facultatively anaerobic rod, oxidase-positive, and motile by a sheathed polar flagellum that exhibited non-fermentative metabolism and required sodium ions for growth. It was not capable of using citrate, fructose, sucrose, sorbitol and glycerol but it was able to utilize mannose and maltose and hydrolyses gelatin. The substance produced by *P. tunicata* has three active components, two are anti-biofilm and anti-fouling proteins and the third is a toxic low molecular weight compound.

Inhibition of QS system can occur by the inhibition of signal generation, inhibition of signal dissemination (degradation or importing), and inhibition of signal reception. AHL signal generation can be inhibited by competitive inhibition with analogs of the amino donor used in the generation of the homoserine lactone ring. Inhibition of signal dissemination can be observed with the degradation of signaling molecules by enzymes produced by a *Bacillus* species. Some bacteria, including the *S. typhimurium* and *E. coli*, are able to import extracellular Al-2 into the cell by transporters, thus eliminating the signal from the environment and rendering it nonfunctional. This creates the illusion of a low-cell-density monospecies environment. Inhibition of signal receptors can be done by competitive and non-competitive inhibitors. Competitive inhibitors are molecular analogs to the signal molecule. Noncompetitive inhibitors show little or no structural similarity to the signal molecule. *S. aureus* strains can be categorized into four groups based on the unique sequence of AIP containing thiolactone. Each AIP stimulates its own QS system and inhibits all of the others by blocking of the sensor kinase AIP-binding domain by the non-analogous AIP. Also, a group II AIP derivative consisting of only the amino acids linked to the thiolactone ring acts as a global inhibitor of all four groups.

XII. Prevention of Fouling

Anti-fouling paints that contain copper, TBT, and other toxic additives have historically been produced to protect marine surfaces from biofouling. These paints containing the additives are usually formulated to expose the toxic materials embedded within the coating structure to the environment. It is this exposure that allows the toxic materials to leach into the marine environment, thus reducing attachment by the marine organisms. However, these additives have a generally adverse effect upon the marine environment.

These biocides caused serious environmental problems in fish, tunicates, mussels, and marine mammals. Although copper is a naturally occurring element it can be poisonous in excess. Copper ions are persistent and accumulate in the environment, therefore, long term use can present a concern. Benthic animals that accumulated copper developed reduced respiration rates and impaired growth in mussels, clams, and other shellfish. TBT based coatings are the most effective yet also the most harmful. According to the Environmental Protection Agency (EPA), TBT is an endocrine disrupting chemical that causes reproductive problems in aquatic animals. Endocrine system disruptors are chemicals that activate or block hormones, interfering with the normal system. Since the 1980s, imposex, the development of male sexual characteristics, has been reported. TBT caused deformities of imposex in gastropods (*Prosobranchia*) (*Marisa cornuarietis*), the mud snail llyanassa obsolete, the whelk *Buccinum undatum* and impacted the clam *Ruditapes decussates*. TBT also caused reduced growth rate in the blue mussel (*Mytilus edulis*), shell hardening in the oyster (*Crassostrea gigas*), mortality in Rainbow trout (*Sa/mo gairdneri*), and impacted a variety of other organisms. High levels of TBT found in marine mammals is evidence that TBT is bioaccumulating in the food chain. TBT suppresses the immune system in mammal. Consequently, the Marine Environment Protection Committee (MEPC) of the International Maritime Organization (IMO) has approved a resolution to phase out and eventually prohibit the use of toxic organotin derivatives in anti-fouling paint. In addition, even where the use of these additives is permitted, the additives are expensive to use, requiring frequent refurbishment (in some regions as frequently as every six months). Also, these toxic additives are costly in terms of both resources and damage to the environment. Moreover, the marine organisms that attach to the underwater surface can acquire an immunity to the toxic materials and effectively render the materials impotent. Thus, there is a compelling need to develop, alternative eco-friendly anti-fouling paints.

The bacterial isolates and/or extracts disclosed herein can be incorporated into marine coatings to limit undesirable marine fouling. The anti-fouling paints offer significant advantages over previous attempts to solve marine fouling problems. For example, the inventive method relies on living cells and/or extracts to prevent biofouling. Thus, the coatings can be formulated so as not to contain toxic materials (such as heavy metals), and still retain their efficacy. This avoids the environmental concerns associated with the use of heavy metal biocides.

The anti-fouling paint may further contain binders(s), pigment(s), solvent(s) and additive(s). Solvents carry the solid components of paint and are used to obtain the desired viscosity and correct consistency. Examples of the solvent include, but not limited to, aromatic hydrocarbons such as xylene and toluene; aliphatic hydrocarbons such as hexane and heptane, esters such as ethyl acetate and butyl acetate; amides such as N-methylpyrrolidone and N,N-dimethylformamide; alcohols such as isopropyl alcohol and butyl alcohol; ethers such as dioxane, THF and diethyl ether; and ketones such as methyl ethyl ketone, methyl isobutyl ketone and methyl isoamyl ketone. The solvent may be used alone or in combination thereof.

The binder or resin is one of the most important components of paint. It is the basic solid film former that remains after the solvent has evaporated and which binds the pigment particles together into a cohesive paint film. The binder determines many of the necessary film properties such as adhesion, gloss level, hardness, abrasion resistance, flexibility, speed of drying and durability. Examples of binders include, but not limited to, alkyd resin, acrylic or vinyl emulsions, polyurethane resins, epoxy resins, silicone based resins, acrylic resins and inorganic silicate based resins. Among the binders which have been used in anti-fouling coatings are vinyl resins, particularly a vinyl chloride/vinyl acetate copolymer, and rosin.

The paint composition can contain one or more pigments. The pigments used in paint are normally present as fine solid particles that are dispersed, but not soluble, in the binder and solvent. Examples of pigments include, but not limited to, titanium dioxide, cuprous oxide, iron oxide, talc, aluminium flakes, mica flakes, ferric oxide, cuprous thiocyanate, zinc oxide, cupric acetate meta-arsenate, zinc chromate, zinc dimethyl dithiocarbamate, zinc ethylene bis(dithiocarbamate) and zinc diethyl dithiocarbamate.

Additive ingredients may optionally be incorporated into the coating composition thus prepared. Examples of the additive ingredients are dehumidifiers, wetting/dispersing agents, anti-settling agents, anti-skinning agents, drying/curing agents, anti-marring agents and additives ordinarily employed in coating compositions as stabilizers and anti-foaming agents. Also, any antibiotic which is toxic to gram negative organisms and which is relatively insoluble in seawater can be used with an anti-fouling marine paint. U.S. Pat. Nos. 4,678,512, 4,286,988, 4,675,051, 4,865,909 and 5,143,545 describe methods for preparing marine anti-fouling paints.

The anti-fouling coatings so produced can be used for the submersible surfaces of boat hulls, pilings, buoys, floating or emplaced offshore platforms, submergence vehicles, navigational aids, and any marine structures where marine biofouling may be a problem.

Biological Deposits

Exemplary isolates have been deposited with St. George's University Microbiology Depository, St. George's University #7, St. George's, Grenada (Dr. Zara Ross, Laboratory Director). St. George's University Microbiology Depository meets the following requirements: (1) it has a continuous existence; (2) it exists independently of the control of the depositor; (3) it possesses the staff and facilities sufficient to examine the viability of a deposit and store the deposit in a manner which ensures that it is kept viable and uncontaminated; (4) it provides for sufficient safety measures to minimize the risk of losing biological material deposited with it; (5) it is impartial and objective; (6) it can furnish samples of the deposited material in an expeditious and proper manner; and (7) it will promptly notify depositors of its inability to furnish samples, and the reason why.

Following is a list of the 24 isolates deposited with St. George's University Microbiology Depository. All of the listed isolates were checked for viability and all were found viable.

TABLE 1

| Strain/Isolate Designation |
|---|
| P1-5 |
| P1-3 |
| P2-1 |
| P2-2 |
| P3-1 |
| P3-2 |
| P3-3 |
| P4-4 |
| P5-1 |
| P5-2 |
| P5-3 |
| P5-4 |
| P6-1 |
| P6-2 |
| P6-3 |
| P6-4 |
| P6-5 |
| P6-6 |
| S1-1 |
| S1-3 |
| S2-1 |
| S2-2 |
| S3-1 |
| S3-2 |

Bacterial cultures of P4-4 and P2-2 were also deposited under the conditions of the Budapest Treaty with the American Type Culture Collection (ATCC, 10801 University Blvd., Manassas, Va. 20110-2209), and are designated PTA-6682 and PTA-6681, respectively. Additional isolates were also deposited under the conditions of the Budapest Treaty with the ATCC, which include P3-2 (PTA-6763), P5-2 (PTA-6764), P6-5 (PTA-6765) and P6-6 (PTA-6766). These biological deposits are exemplary of the disclosed isolates.

EXAMPLES

Example 1. Sampling of Coral Reef Fish

The reef fish, *Sparisoma ninidae* (Parrotfish) and *Lutjanus purpureus* Red Snapper) were caught above a coral reef in True Blue Bay, Grenada at N=11° 59.908 and W=061° 46.282 in accordance with a Global Positioning System (GPS) (GEKO 201 Garmin Taiwan). Fish were either trapped in a fishpot or shot with a spear gun. The fishpot used to trap the fish was made of 0.5 inch galvanized square mesh, 36 inches long, 16 inches wide and high. The cornucol hole (horn shaped) on one side of the fishpot was 7 inches in diameter on the outer surface and it tapered inside the fishpot to a 5 inch diameter. The fishpot was located approximately 10 feet deep, next to a coral reef, approximately 150 feet away from shore. At the surface after caught, each fish was washed twice with autoclaved artificial seawater to remove any loosely associated microbes and then immediately placed in a sterile plastic bag on ice. The fish was then transported back to the laboratory.

Example 2. Isolation of Pure Cultures from the Epithelial Mucosal Surfaces of Coral Reef Fish Normal fish microflora was collected from the mucus surface of the fish with a sterile cotton swab and plated on Artificial Sea Water Agar (ASWA) medium. ASWA medium was used to mimic fish mucus. Artificial Sea Water Agar (ASWA) contained (g/l) of solution: NaCl 21.10, KCl 0.58, $CaCl_2 \times H_2O$ 1.20, $MgCl_2 \times 6H_2O$ 4.73, $NaHCO_3$ 0.08, $MgSO_4 \times 7H_2O$ 2.63, yeast extract 10.00, malt extract 4.00, glucose 4.00, agar 15.00. Solution was adjusted to pH 7.5-8.0, autoclaved at 121° C. for 20 min, and poured into sterile Petri dishes. Artificial Sea Water (ASW) liquid broth was prepared as above except the 15.00 g of agar was omitted.

Plates were incubated at 29° C. for 48 hours. Separate colonies were picked, inoculated and grown in the same liquid medium and cultured under the same temperature for 48 hours. Then the cultures were plated again on the solid ASWA. Gram staining was done to ensure that cultures were pure. Photography of isolates was done using an Olympus BX41 Microscope with a Polaroid DMC camera and Olympus U-TUIX adapter, using Paintshop Pro software. Alternatively, light microscope pictures were taken of the isolates using a digital camera (Powershot Canon digital camera A620), Carl Zeiss adapter, and Axioscope 20 Zeiss Microscope (Model Number 451487). The cultures were frozen in ASW suspension with glycerol (1:2) at −70° C. for further experiments in small cryogenic vials (1.5 ml) (NUNC, Fisher Scientific).

Fifteen microorganisms were isolated from six *S. ninidae* and five microorganisms from three *L. purpureus* (Table 2). Fish culture collection was created and catalogued as the following: species name, strain designation, isolation source, medium, name of researcher, physiology, biochemistry, and biotechnologically important properties (for example, producer of unidentified antibiotic, or anti-fouling agent). The letter P was used to designate the isolates from the Parrotfish, followed by a number representing the fish, a dash and a number representing the isolate. In the same manner, the letter S was used to designate the isolates from Snapper (Table 2).

Reference microorganisms were grown on suggested media and cultivation conditions according to the instructions of the vendor or depository, such as the ATCC. *Psychrobacter immobilis* and *P. phenylpyruvicus* were cultivated on Brain Heart Infusion (BHI) broth (Difco 237500) and BHI agar (Difco 241830) at 26° C. *Marinobacter hydrocarbonclasticus* was cultivated on Marine Broth 2216 (BO 279110) and Marine Agar 2216 (BO 212185) at 30° C. *Aerococcus viridans* and *Desemzia incerta* were cultivated on Brain Heart Infusion broth (Difco 0037) and Trypticase Soy Agar (BBL 11043) with 5% defibrinated rabbit blood 37° C.

*Staphylococcus warneri* and *Serratia marcescens* was cultivated on Nutrient broth (Difco 0003) and Nutrient agar (Difco 0001).

Example 3. Morphological and Physiological Characterization of Isolates

Morphology of the cells from the isolates was studied after Gram-staining using phase contrast microscopy. Blood agar, Mannitol salts agar, Mac Conkey Agar, and Cysteine tryptic agar were used to test type of hemolysis, acid production from mannitol, resistance to bile salts, and oxidation/fermentation of glucose, respectively. Catalase reaction and oxidase reaction were performed using traditional techniques known in the art.

Twelve of the fifteen parrot fish isolates were gram positive, eight were cocoidal, and ten were pigmented. Three of the five snapper isolates were gram positive, four were cocoidal, and four were pigmented. The majority of the isolates were gram positive and pigmented (Table 3). Most of the isolated organisms were aerobic, heterotrophic, halotolerant, and mesophilic (Table 4). All of them grew best at 28° C. and salinity of 40 ppt, however, fifteen could grow at 37° C. with salinity of 8 ppt (Table 4). Isolate P6-1 and P6-2 were 13-hemolytic. Of the Gram-positive cocci tested on Mannitol Salts Medium, isolates P3-1, P3-2, P1-5, and P2-2 produced acid from mannitol at salinity of 75 ppt indicating that they may be pathogenic Staphylococci. Majority of strains were resistant to bile salts at 28° C. tested on Mac Conkey Agar. P3-2 and S1-3 oxidized and fermented glucose, S1-1 was able to ferment glucose only, and P4-4 and P5-2 were unable to use glucose tested on Cysteine trypic agar. Catalase test showed that fourteen isolates were catalase-positive. Oxidase test showed that eleven isolates were oxidase-positive.

Isolate P3-1 and P3-2 were Gram-positive cocci, 1-3 µm, halophylic, mesophilic (28-37° C.), consumed mannitol, and did not contain cytochrome-oxidase. Isolate P3-1 was transparent, catalase-negative, and gamma-hemolytic, while P3-2 produces a white pigment, was catalase-positive, alpha-hemolytic, and its generation time at salinity of 40 g/I for P3-2 was 7.35 hours. Isolates P1-5 and P2-2 were gram positive cocci, 1-2 µm, without colony pigmentation, non-motile, halophilic, mesophilic (28-37° C.), catalase-negative, alpha hemolytic, oxidase-negative, and produced acid from mannitol. Isolate P5-2 was Gram-positive cocci, 1-4 µm, orange pigmented, non-motile, halophilic, mesophilic (28-37° C.), its generation time at salinity of 40 g/I was 1.38 hours, alpha hemolytic, oxidase-positive, catalase positive and it did not consume mannose. Isolate P4-4 was a Gram-positive motile coccobacilli that grew at 28-37° C. P4-4 did not use glucose, it was catalase-positive, and oxidase-positive.

Example 4. Growth Curves for Isolates P4-3, P5-2, and P3-2

Growth curves were created for isolates P4-3, P5-2, and P3-2 by measuring optical density (OD) using a spectrophotometer (Spectronic 20 Bausch and Lomb). These isolates grew in ASWA as described above but excluding agar, at 29° C., pH 8.0, and salinity 40 g/I until stationary growth phase was observed. Number of generations using OD growth curves was calculated with the following equation: n=3.3 (log N-Log No) where N and No are two different Klett values between time interval t. Generation time was calculated with the following equation: g=t/n. Growth rate constant was calculated with the following equation: k=ln 2/g.

The growth curves were obtained at 29° C., pH 7.5-8.0, in ASWA. Growth curves are typical for bacteria. Growth begins at a slow rate with the lag phase, then at a fast exponential rate with the log phase, and finally growth stops with the stationary phase. The latter is when secondary metabolites are produced by the bacteria, thus, extracts were taken from bacteria at this phase.

OD turbidity measures both live and dead cells thus, OD based growth curves over estimates the number of cells. OD reproduces growth curves accurately, however, and underestimates time line for the stationary phase by several hours. Generation time for P4-4, P5-2, and P3-2 are 2.53 hrs, 1.38 hrs, and 7.35 hrs respectively. Growth rate constant for P4-4, P5-2, and P3-2 are 0.274, 0.502, and 0.094 respectively. Largest OD was observed with isolate P4-4 and longest generation time was observed with isolate P3-2 (FIG. 1).

Differences were observed because isolates were not grown at optimum conditions. After 48 hours each bacteria was in stationary phase of growth.

Example 5. Antibacterial Activity of Microbial Extracts

The isolated organisms were grown in 500 ml flasks containing ASW medium in a shaker bath at 29° C. at 180 revolutions per minute (RPM) for 48 hours. The cells were separated from the culture medium by centrifugation at 5,000 RPM for 20 minutes in 50 ml centrifuge tubes. The cells were washed twice by additional centrifugation with ASWA to ensure removal of supernatant. Crude extracts were obtained from the supernatant culture medium. First, hydrochloric acid (HCl) was added to supernatant to lower pH to 2.0. Supernatant was then shaken with an equal aliquot of diethyl-ether for 5 minutes. After ten minutes standing, the bottom portion was removed and discarded. The ether portion was shaken for 5 minutes with EDTA buffer at pH 8.0 to re-extract the metabolites into the water. After ten minutes of standing, the bottom portion of crude extract was collected in sterile containers and the ether portion was discarded. Also, in some cases, the final ether portion was left open to evaporate the diethyl-ether. Then, 70% alcohol was added to re-suspend extract.

Sterile disks (6 mm diameter) were soaked in the extracts and placed on Nutrient Agar (NA) plates freshly inoculated with a reference organism to determine if secondary metabolites, produced by the isolates during their stationary phase of growth, resulted in the inhibition of bacteria. Reference strains: *S. aureus* ATCC 25923, *S. saprophiticus* ATCC 15305, *S. epidermidis* ATCC 12228, *Micrococcus* spp., *E. cloacae* ATCC 23355, *S. marcescens* ATCC 8100, *S. sonnei* ATCC 25931, *K. pneumoniae* ATCC 13883, *P. vulgaris* ATCC 13315, and *S. typhimurium* ATCC 14028 were used for the antibacterial tests. Controls disks were soaked with extraction buffer treated with diethyl ether and placed on same plate. The plates were incubated at 37° C. for 48 hours. Diameter of clearance zones around disks were measured in mm and compared to the controls. Diameter of clearance zones around disks exceeding 6 mm was considered as an indication of antibacterial activity of an extract.

The results showed that 87.5% of the fish extracts were active against at least one of the reference strains (Table 5). The strongest antibacterial activity was observed with extracts from mucus producing isolates P6-5 and P6-6 against *S. aureus* (FIG. 3), *S. epidermidis*, *K pneumoniae*, and *P. vulgaris*. Three of the isolates (P1-5, P2-2, and P3-1) showed activity in both antibacterial tests. Isolate P3-2 did not show activity in the antibacterial extract test. These results demonstrate that secondary metabolites produced by the isolates during their stationary phase of growth result in the inhibition of bacteria.

Example 6. Antibacterial Effect of Living Cells

Reference organism (see Example 5) and fish isolate were cross streaked on top of the other on NA plate and incubated at 37° C. for 48 hours. Clearance zones of inhibited growth for reference organism were measured and recorded in mm as width of the inhibition streak band. A zone of clearance of 1.0 mm and larger indicates a positive result of inhibition.

33.3% of the fish isolates tested showed antibacterial activity against two of the nine reference strains tested, *S. aureus* and *S. epidermidis* (Table 5). Five isolates (P5-1, P5-2, S1-1, P3-3, S2-1, P5-3, S3-2, and S2-2) did not show antibacterial activities in the streak test. These results indicate that living cells of the fish isolates inhibited the growth of reference strains.

Example 7. In Situ Inhibition of Fouling by Isolates P5-2, P3-2 and P4-4

Slides incorporated with extracts, living cells, and controls were deployed into the sea to determine if the secondary metabolites and living cells were active in situ against bacteria and eukaryotic organisms in the sea. Crude extracts (20 µl/slide) or washed cells ($10^5$ to $10^7$ cells/ml) were incorporated into gels (Phytagel 3.26%) on sterile, chemically cleaned glass slide. Crude extracts were obtained in the same manner as for antimicrobial experiments with the exception of using distilled water at pH 8.0 for the re-extraction, instead of EDTA buffer. Control slides were covered with Phytagel prepared with sterile extract controls. Treatments and controls were done in triplicates.

The gel covered slides were attached to rubber stoppers and exposed to the seawater at a depth of 1 meter below the surface in True Blue Bay, Grenada, at N12° 00.040 and W061° 46.177 for 24 hours. Experimental slides were screened for biofilm formation and eukaryotic fouling and compared to controls. Slides were stained with acridine orange and observed under a UV microscope (Carl Zeiss Axioscope equipped with UV lamp with LP 420 excitation filter).

Individual bacterial cells, area of microcolonies, and eukaryotic organisms (larger than 10 µm) with or without chlorophyll were counted on ten fields per slide. Numbers for the three sets of slides were compiled and used for statistical analysis using a two-tailed t-test using Microsoft Excel. For the slides deployed with living cells the number of bacteria added prior to deployment into the water was not subtracted from the count after 24 hours, thus, quantification of bacteria was overestimated and biofilm inhibition was underestimated.

Water samples were taken from the water column immediately above the area where slides were deployed. Temperature, pH, salinity, dissolved oxygen (DO), and biological oxygen demand (BOD) were measured in the water samples using standard methods known in the art. Conditions of water directly above slide location yielded salinity of 30 ppt, pH at 7.8, temperature of 31° C., and DO at 3.78 mg/L. BOD data ranged from 1.49-3.09 mg/l with SD 14-43% over a period of two weeks.

Figure 2:
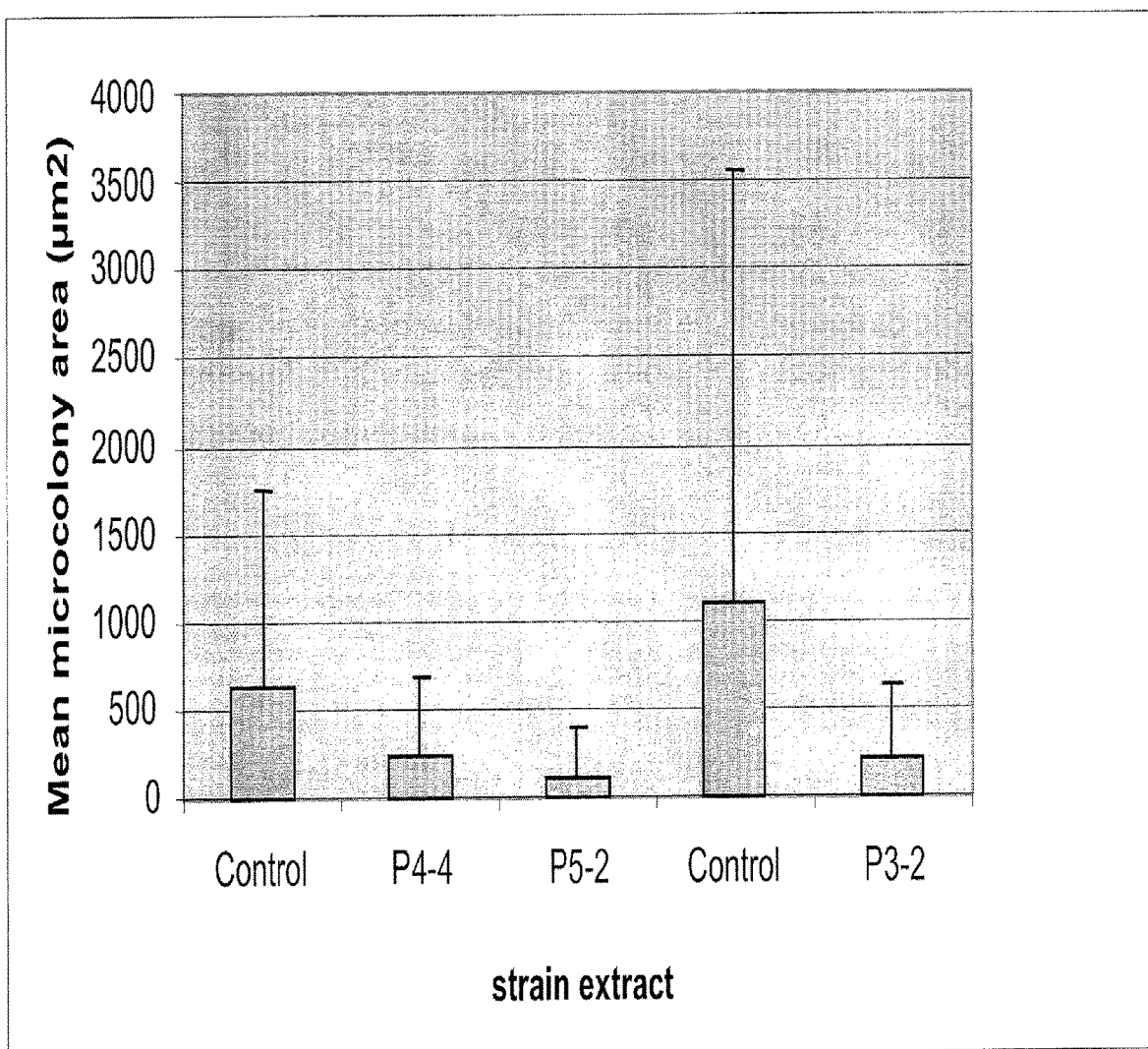
FIG. 2. This figure is a bar graph showing in situ inhibition of bacterial settlement by microbial extracts of strains P4-4 ($p=0.099$), P5-2 ($p=0.024$), and P3-2 ($p=0.061$) compared to respective controls. A single control was used for strains P4-4 and P5-2.

75% of the tested extracts showed anti-biofilm forming activity and 25% showed anti-eukaryotic activity. The inhibition of biofilm formation was observed with extracts from isolates P5-2 (84.5%), P3-2 (82.0%), and P4-4 (63.2%) when compared to controls (FIG. 2, Table 7). Highest biofilm inhibition was observed with extracts from strains P5-2 and P3-2.

Isolate P5-2, *S. warneri*, was not bacteriocidal against the pathogenic reference strains, however, it produced the greatest percent reduction of biofilm formation with 84.5% (Table 7). This indicates that *S. warneri* either produced a signaling compound, an AIP or AI-2 similar to other *Staphylococcus* species including, *S. epidermidis* or *S. aureus* and was responsible for the observed inhibition. *S. warneri* also may have induced inhibition of QS by blocking signaling molecules or removing them from the environment as described elsewhere in the application.

Figure 3:
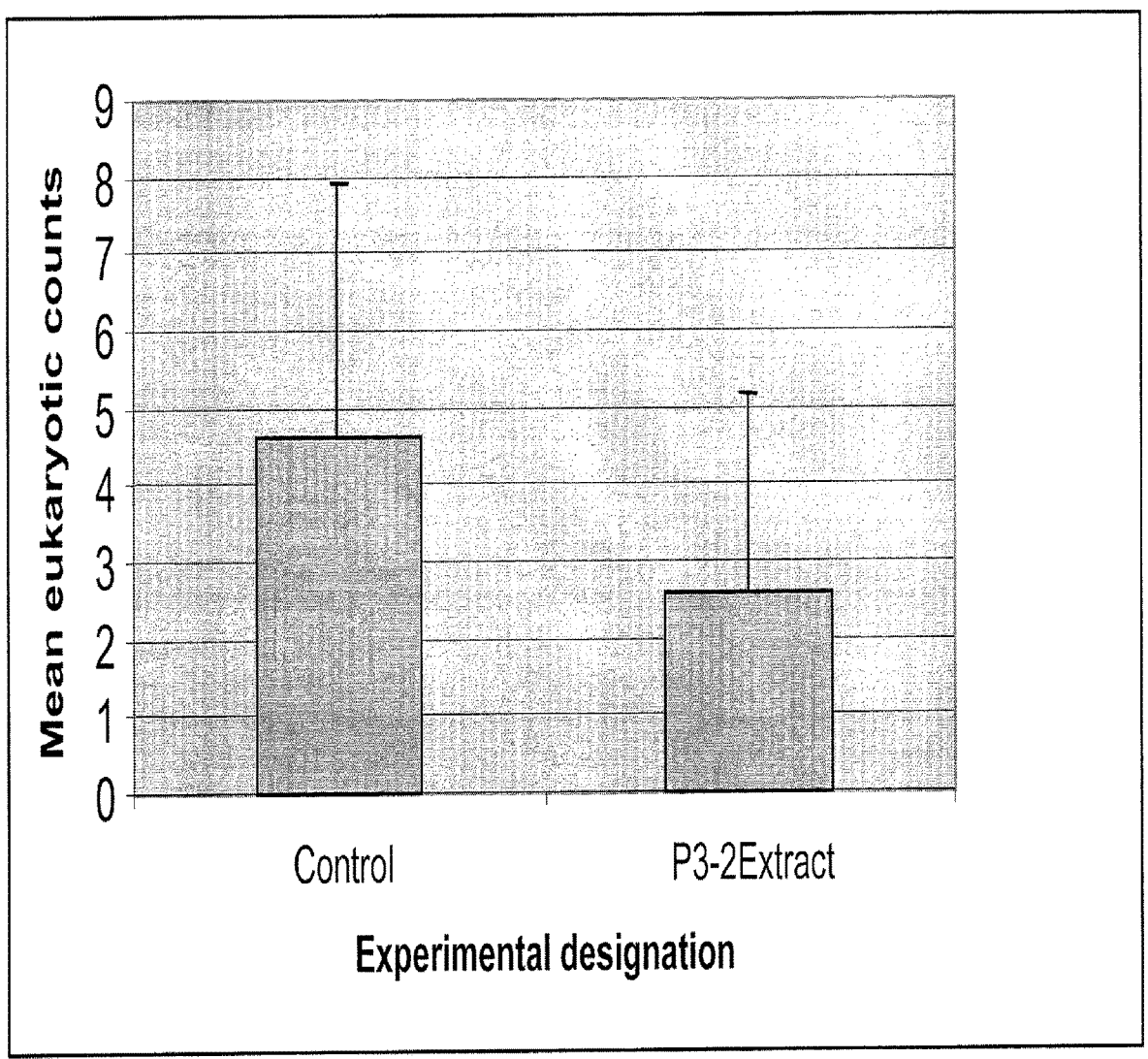
FIG. 3. This figure is a bar graph showing in situ inhibition of non-photosynthesizing eukaryotic cells at 45.4% by P3-2 Extract ($p=0.0086$) compared to respective control.
Figure 4:
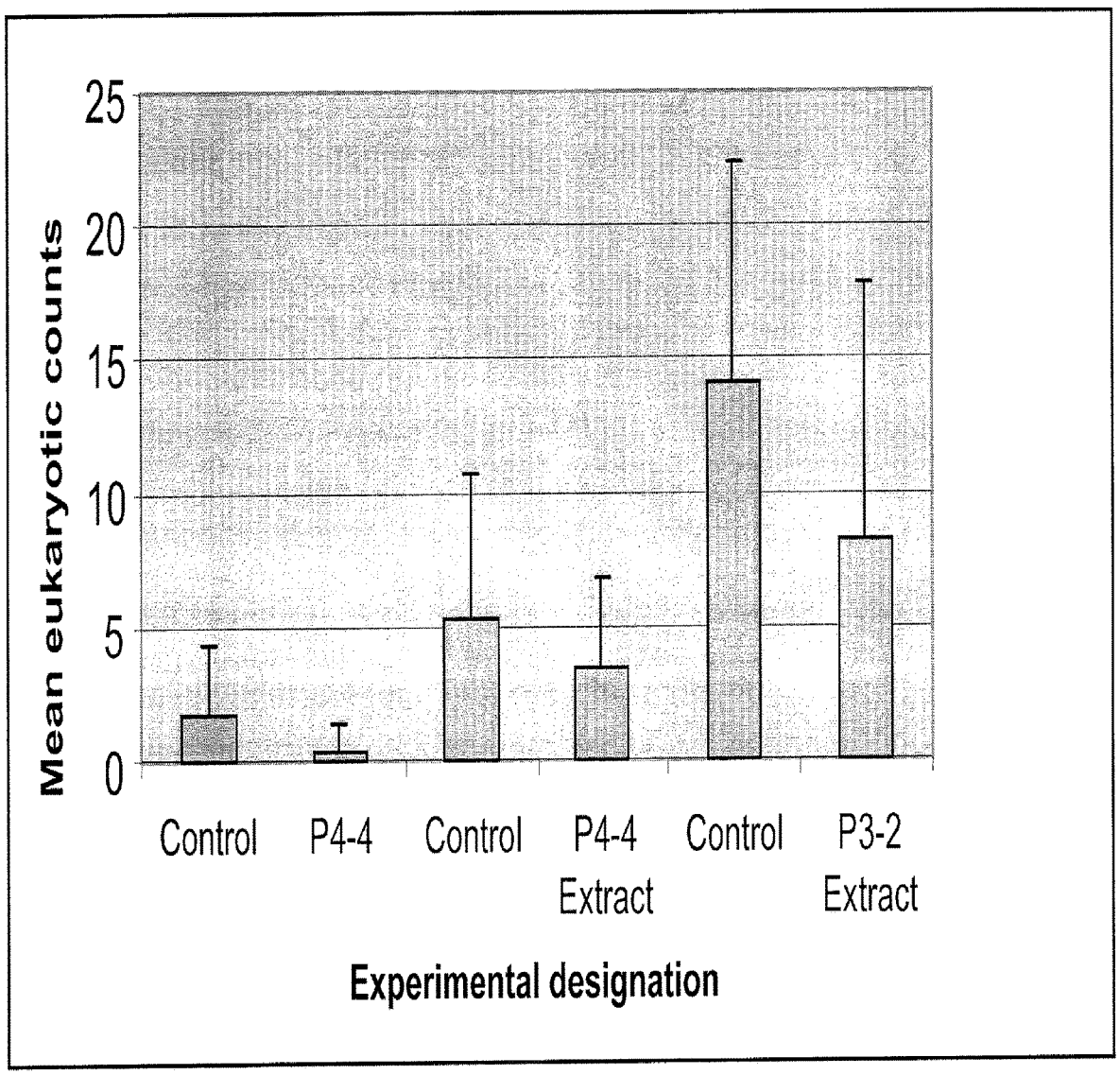
FIG. 4. This figure is a bar graph showing in situ inhibition of photosynthesizing eukaryotic cells at 41.7% by P3-2 Extract ($p=0.013$), 36.5% by P4-4 Extract ($p=0.094$), and 78.2% by P4-4 living cells ($p=0.009$) compared to respective controls.

Non-photosynthesizing eukaryotic inhibition was observed with extracts from strain P3-2 (45.4%) (FIG. 3, Table 7). Photosynthesizing eukaryotic inhibition was observed with extracts from isolates P3-2 (41.7%) and P4-4 (36.5%) and living cells of isolate P4-4 (78.2%) (FIG. 4, Tables 6 and 7). A larger percentage of inhibition was observed against photosynthesizing eukaryotic organisms. The isolates were taken from reef fish that inhabit water in the photic zone, exposed to light, therefore, it would be beneficial for the bacteria on their surfaces to be more antagonistic towards photosynthesizing organisms.

These results demonstrate that secondary metabolites produced by the isolates from epithelial mucus of reef fish significantly inhibit both bacterial and eukaryotic fouling.

Example 8. Identification of Active Anti-Fouling Isolates Using Fatty Acid Analysis and 16S rRNA Gene Sequencing Six isolates, P3-2, P4-4, P5-2, P1-5, P2-2 and P3-1, were identified using Fatty acid identification in bacterial membranes analysis (FA) and sequencing (526-535 bp) of 16S rRNA gene. FA and 16S rRNA gene sequencing were done in Microbial ID Labs (Newark, Del.). FA analysis results are based on Similarity Index (SI), a value that represents the comparison of FA composition of an unknown microorganism to the mean FA compositions of the strains used to create the library entry listed as its match. The search gives the best database matches with respective similarity indices. According to this test, an exact match yields a similarity index of 1.000. A similarity of 0.600 is a good species match, similarity between 0.400 and 0.600 may be a species match, indicating an atypical strain. A similarity index lower than 0.400 suggests that FA isolate composition is not represented in the database.

16S rRNA sequence analysis was performed using Applied Biosystems MicroSeq™ microbial analysis software and database to obtain the top ten matches. Matches are presented in a percent genetic distance (low percentage indicates a close match). Neighbor joining phylogenetic trees were made using the top ten matches.

Comparison of fatty acid profiles of the isolates P1-5 (0.386) and P2-2 (0.367) showed that both may represent a new species, distantly related to *D. incerta* (Table 8). *D. incerta* is associated with ovaries of insects and closely related taxa are associated with common seals.

Comparison of fatty acid profiles of the isolate P3-1 (0.523) and P3-2 (0.554) and additional comparison of 16S rDNA of strain P3-2 to database (99.72%) showed that both of them are related to *A. viridans* (Table 7). *A. viridans* is known to be a Gram-positive tetracocci. It was associated with lobster in Maine, urinary tract infections, and endocarditis in humans. P3-1 and P3-2, also showed differences with each other, P3-1 was catalase-negative and gamma-hemolytic, while P3-2 was catalase-positive and alpha-hemolytic, indicating that they may be different strains of A. viridian or new species.

Comparison of 16S rDNA of strain P5-2 to database showed it was closely related to *S. warneri* (100% match) (Table 8). *S. warneri* was previously described as associated with human skin, and the foregut of an insect, and human adenocarcinoma of the breast. It was reported to cause bacteremia, infective endocarditis, cerebrospinal fluid shunt infection, subdural emphysema, vertebral osteomyelitis, and urinary tract infections. This indicates that *S. warneri* is a good biofilm former. Isolate P5-2 differs from type strain of *S. warneri* (ATCC 10209) because it was oxidase-positive, thus P5-2 may be a new strain.

Figure 5:
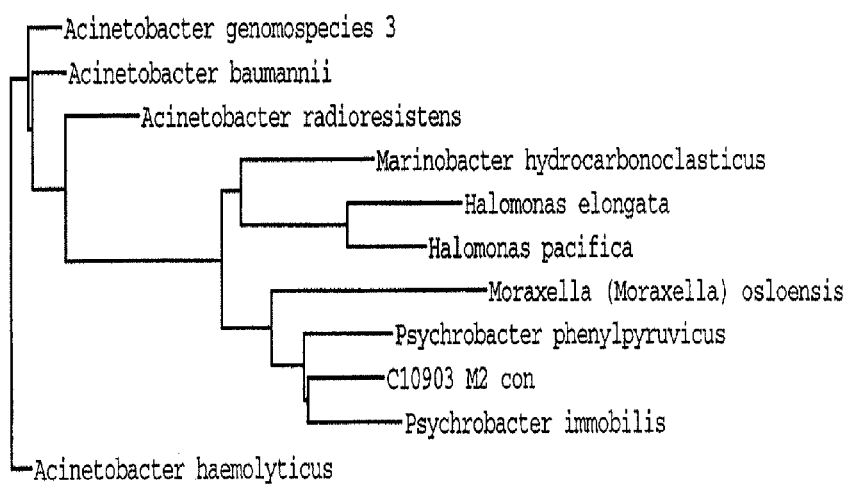
FIG. 5. This figure is a phylogenetic tree showing relatedness of strain P4-4. Isolate P4-4 is distantly related (94.85%) to *P. immobilis* and (94.73%) to *P. phenylpyruvicus*.

Comparison of 16S rRNA of isolate P4-4 to database found no match for this isolate except that it was distantly related (94.85%) to *P. immobilis* and (94.73%) to *P. phenylpyruvicus* (FIG. 5 and Table 8). *P. immobilis* was associated Antarctic coastal marine environments, poultry carcasses, and rainbow trout. *P. immobilis* was Gram-negative non-motile coccobacilli that did not grow at temperature higher than 37° C., used carbohydrates, and tolerated 5% bile salt. P4-4 differs from *P. immobilis* because it was motile and did not utilize glucose. P4-4 had a greater than 5% difference in 16S rRNA gene sequencing and FA analysis produced values less than 0.4 indicating that isolate P4-4 represents a new species or a new genus (Table 8).

Example 9. Prevention of Biofilm Formation by Anti-Fouling Marine Paint

A sterile, chemically cleaned glass slide can be painted with a regular paint (e.g., Interlux® Perfection, Product No. YHB000) to which the extracts produced by the isolates P3-2, P4-4 and P5-2 are added (2% by weight). A slide coated with just the regular paint can be used as a control. Slides can be deployed into the sea for 24-48 hours to test the anti-biofilm activity of the paint containing the extracts. The results will show that the slide coated with the paint containing the extracts prevents the formation of a biofilm on its surface.

Example 10. Prevention of Fouling by Anti-Fouling Marine Paint

A designated area on the side of a boat can be painted with a regular paint to which the extracts produced by the isolates P3-2, P4-4 and P5-2 are added (see Example 9). Another area painted with a regular paint without the extracts can be used as a control. The boat can be deployed into the water for a month and observed for fouling. The results will show that fouling was inhibited on the surface of the boat coated with the paint containing the extracts.

Example 11. Detachment of Biofilm Formers in Microtiter Wells by Extracts of Isolates To develop biofilms, 25 µL of stationary growth phase *S. aureus* bacterial culture (requiring about 18 h growth at 37° C. in TSB 2% and containing about $2 \times 10^9$ cells/ml) can be added under aseptic conditions to a well of a tissue culture-treated polystyrene 96-well plate (cell well tissue culture treated polystyrene plates; Corning, Rochester, N.Y.), containing 175 of growth medium (TSB 2%). Biofilms can be developed (at 37° C.) for 6 or 48 h, the growth medium being discarded and freshly added every 12 h. Each well can be washed three times with phosphate-buffered saline (PBS) under aseptic conditions to eliminate unbound bacteria, and 200 µL of the P5-2 extracts can be added, the mixture being maintained at 37° C. After 3, 6 or 24 hours extract solutions can be removed with a micropipette and wells can be filled (200 µL) with undiluted dimethyl sulphoxide (DMSO; Panreac, Barcelona, Spain), which can be used as ATP extractant.

Plates can then be wrapped in plastic and placed in a sonicator bath (P-Selecta, Barcelona, Spain) for 15 min (in the case of 6 h biofilms) or 30 min (in the case of 48 h biofilms) at 40 Hz and 22-24° C. to favor the disintegration of bacterial clumps. The number of viable bacteria can be estimated by measuring the amount of ATP present in the sample using ATP-bioluminescence. The results will show that extracts from P5-2 isolate decreased the *S. aureus* biofilm cell viability indicating the anti-biofilm activity of the extracts.

The extract solutions can be used to measure cell turbidity, using a UV spectrophotometer, at an optical density at 595 nm ($OD_{595}$). The average OD of the control wells can be subtracted from the OD of all test wells. The result will show that bacterial cells are present in the extract solution indicating that biofilm forming cells have detached from the surface of the wells after the addition of the microbial extracts.

Example 12. Microtiter Plate Assay for Assessment of Activity of Microbial Extracts on Biofilm Formation Strains of *S. aureus* and *P. auriginosa* can be grown overnight in 5 ml test tubes at 32° C. in respective media. Overnight cultures can be transferred (0.1 ml) to 10 ml of minimal defined media using glucose as the only carbon source and vortexed. After vortexing, 100 volumes can be transferred into microtiter wells in a PVC microtiter plate. 200 µl of extracts produced by the isolates P3-2, P4-4 or P5-2 (see Example 5) can be added to each well. Plate can then be rinsed with 70% alcohol and air dried. 8 wells of media without bacteria can be included in each plate and used as control wells. Plates can be incubated and covered at 32° C. for 40 hours.

The medium can be removed with a micropipette and cell turbidity can be measured, using a UV spectrophotometer, at an optical density at 595 nm ($OD_{595}$) after 40 hours. The average OD of the control wells can be subtracted from the OD of all test wells. The microtiter wells can then be washed five times with sterile distilled water to remove loosely associated bacteria. Plates can be air dried for 45 min and each well can be stained with 150 µl of 1% crystal violet solution in water for 45 min. After staining, plates can be washed with sterile distilled water five times. At this point, biofilms will be visible as purple rings formed on the side of each well. The quantitative analysis of biofilm production can be performed by adding 200 µl of 95% ethanol to detain the wells. 100 µl from each well can be transferred to a new microtiter plate and the level (OD) of the crystal violet present in the destained solution can be measured at 595 nm to determine the amount of biofilm formed.

The results will show that the amount of biofilm formed in the wells treated with microbial extracts will be lesser when compared to the control wells. These results demonstrate the anti-biofilm activity of the extracts.

Example 13. Detachment of Biofilm from Hydrophobic and Hydrophilic Chips

Strains of *S. aureus* and *P. auriginosa* can be grown overnight in 5 ml test tubes at 32° C. in respective media until $OD_{600}$ of between 0.6 and 0.7 can be observed. Seven milliliters of the bacterial suspension can be poured into a Petri dish (55-mm diameter) containing a chip (3 by 1 cm) of stainless steel (hydrophilic) and polytetrafluoroethylene (PTFE, hydrophobic) and incubated at 32° C. for 2 days. The medium can be replaced after 2 h and 24 h. After 40 hours of biofilm development the supernatant can be removed and the extracts produced by the isolates P3-2, P4-4 or P5-2 (see Example 5) can be added. Controls can be made without extracts.

Each chip/slide can be placed in a Petri dish (90-mm diameter) and washed twice for 1 min each with 35 ml of sterile tryptone salt (TS) (Bacto-tryptone, 0.1%; NaCl, 0.85%) to remove nonadherent cells. Sessile cells can be fixed on the support with a solution of 3% glyteraldehyde in 0.2M cacodylate buffer (pH 7.4) and rinsed in the same buffer. Samples can be stained for 3 min with a solution of 0.05% acridine orange and then washed twice for 1 min with demineralized water. The chips can then be dried in the air for 1 h and observed with a UV microscope to determine the percentage of surface contaminated. The area covered by the biofilm can be converted into a percentage of the total area.

The results will indicate the detachment of bacteria from the surface of the chips treated with extracts. No detachment of bacteria will be observed from the controls. These results will demonstrate that stainless steel and PTFE surfaces commonly used in food-processing plants can be coated with the microbial extracts to prevent the formation of biofilms.

Example 14. Activity of Extracts in a Flow Cell with Marine and Medical Biofilm Formers Biofilms can be grown in glass capillary tubes under continuous flow conditions. The glass tubes can be square cross sections, allowing direct microscopic observation of the biofilms growing on the inside of the tubes through the flat tube walls. The capillaries can be mounted in a flow cell holder to reduce breakage. The capillaries can have a nominal inside dimension of 900 μm and a wall thickness of 170±10 μm (Friedrich & Dimmock, Millville, N.J.). The flow cell apparatus can consist of a vented medium feed carboy (4-liter capacity), a flow break, a filtered air entry, a peristaltic pump, the capillary and flow cell holder, an inoculation port, and a waste carboy. These components can be connected by silicone rubber tubing. The system can also contain a T connector just upstream of the glass capillary to allow mixing of the air as medium flows to enhance the development of biofilm cell clusters of $P.\ aeruginosa$. Medium and system components can be sterilized separately by autoclaving and then connected after cooling in a biological hood.

The capillary flow system can be inoculated with 2 ml of an overnight culture of $P.\ aeruginosa$ with an optical density at 600 nm of 0.001 to 0.005. For inoculation, the flow can be stopped and the tubing can be clamped downstream of the inoculation port. The inoculum can be injected via the port to fill the glass capillary. The tubing upstream of the glass tube can be clamped, and the system can be allowed to stand without flow for 24 h. After this time, the flow of medium (1/10-strength TSB) can be initiated at a flow rate of 20 ml hi. Air can be pumped through the capillary at the same flow rate as the medium by use of a parallel tube in the same peristaltic pump. This can result in slug flow of the medium and air bubbles through the capillary tube. Microbial extracts produced by the isolates P3-2, P4-4 and P5-2 can be added to the system and allowed to flow for 24 hours. Another similar system without the extracts can be used as a control. Biofilm formed can be counterstained by injecting a solution of rhodamine B at 50 mg liter$^{-1}$ into the capillary.

Biofilm can be observed by scanning confocal laser microscopy after 24 h of continuous flow at 37° C. Confocal scanning laser microscopy can be performed with a Leica TCS NT confocal scanning laser microscope, with excitation at 488 and 568 nm and with emission collected at 500 to 530 nm (green channel) and 585 to 615 nm (red channel). Microscope images can be analyzed by use of the line-scan function of MetaMorph image analysis software (Universal Imaging Co., Downingtown, Pa.). The results will indicate the detachment of bacteria from the surface of the capillary glass tube pumped with the medium containing the extracts. No detachment of bacteria will be observed from the controls.

Example 15. DNA Analysis of Isolates DNA Extraction

Cells were grown in 250 ml or 50 ml liquid media or scraped off agar plate. Approximately 1.0 ml of cells was collected in a 1.5 ml microcentrifuge tube. Liquid cultures of cell were pelleted to remove remainder of liquid. Pellet was resuspended in 0.5 ml 1.25 TAE. Suspension was frozen. Once frozen, 0.05 ml of 250 mM Tris and 0.05 ml of 10 mg/ml lysozyme was added and allowed to thaw and placed on ice for 45 minutes. Then 0.1 m of 0.5% SOS and 1.25 TAE, as well as, 40 μl of Proteinase K was added and microcentrifuge tube was heated to 50° C. for 60 minutes. Following this, to precipitate the protein, 0.1 vol 3M sodium acetate was added and microcentrifuge tube, mixed gently and to remove unwanted salts from the DNA and precipitate the DNA, 2 vol 95% cold ethanol was added and mixed by inverting. Microcentrifuge tubes were centrifuged at 8000 rpm for 1 minute. The top portion was discarded and 0.5 ml 50 mM tris and 1 mM EDTA, and 40 μl of 10 mg/ml RNase A was added and dissolved by rocking overnight at 4° C. Subsequently, 0.1 vol 3M sodium acetate was added and microcentrifuge tube was mixed gently and 2 vol 95% cold ethanol was added and mixed by inverting. Microcentrifuge tubes were centrifuged at 8000 rpm for 1 minute. The top portion was discarded and 0.5 ml was added and dissolved by heating to 50° C. for 60 minutes. DNA was diluted using 50 mM Tris 1 mM EDTA. Purity was checked in quartz cuvettes in spectrophotometer (Cary 4000 UV-Vis spectrophotometer, model #EL04123231, with oxygen to remove condensation, and stir control on) with magnetic stir bars at 260 nm and 280 nm using Cary Win UV software. The absorbance of each pair of closely related species was adjusted to be the same by using the buffer 50 mM tris and 1 mM EDTA.

DNA Isolation

The purity of DNA was determined for the isolated DNA (Table 9). The ratio of DNA (A260) to protein (A280) calculated for each isolate and reference organism to determine purity of DNA. Values between 1.8 and 2.0 are considered pure in 10 mM Tris-HCl. The purity of the isolated DNA range from 0.97 to 2.13, however, the majority of DNA fell within the range considered to be pure.

GC Content Determined by Melting Curve

DNA melting curves were created for each isolate and closest related species. The Tm was determined from the graph. Analysis of the G+C content was carried out by measuring the absorbance of 1000 μl of DNA in quartz cuvettes at 260 nm at intervals (Cary 4000 UV-Vis spectrophotometer, model #EL04123321) as temperature increases. Oxygen was used to remove condensation on the cuvettes and magnetic stir bars were used in cuvettes to maintain homogenicity. The start temperature was 15° C. and the rate of temperature increase was 0.5° C./minute until the temperature of 90° C. Data interval was set to collect at the same rate as increase. A separate cuvette was used as a probe to monitor the temperature. Cary Win UV Thermal software was used and converted to Excel. In excel DNA melting curves were created and melting temperatures (Tm) were calculated. % (G+C) were determined using the following equation:

$$\%(G+C)=2.44(Tm-69.4).$$

Once Tm was determined from the graph, the equation was applied and % (G+C) was determined. The % (G+C) was adjusted for the reference cultures with known GC content and the isolates were subsequently adjusted accordingly (Table 9). The % (G+C) differed between all marine isolate and closest related species. All of the % (G+C) results for reference organisms were lower than expected (data not shown), therefore, the % (G+C) for the marine isolates were adjusted using the known GC content for reference organisms (data not shown). The differences in % (G+C) between marine isolate and closest related species, after adjustment, ranged from 0.69 (between P4-4 and *P. immobilis*) to 13.38 (between *S. warneri* and P5-2).

DNA-DNA Hybridization Determined by Percent Hybridized after Re-Cooling

The absorbance of the DNA from the marine isolates and closest related species was checked to ensure that they gave approximately the same reading. DNA from the marine isolates (500 μl) and closest related species (500 μl) were combined in quarts cuvettes. The re-cooling start temperature was 90° C. and the rate of temperature decrease was 0.1° C./minute until the temperature of 15° C. The rate of cooling was chosen because preliminary data revealed that cooling at 0.5° C./minute did not give strands of DNA enough time to re-anneal. Data interval was set to collect at the same rate as increase/decrease. Cary Win UV Thermal software was used and converted to Excel. The initial absorbance at 15° C. was compared to the final absorbance at 15° C. and the ratio was used to determine percent hybridization.

Percent of DNA-DNA hybridization between the closest related species was determined by the ratio of absorbance at the final temperature to absorbance at start temperature (data not shown) related to parts per hundred. Percent hybridization was adjusted using the rate of re-association (between approximately 24° C. to 15° C.) for reference organisms with closest related species (data not shown). The adjusted percent hybridized ranged from 100% (P3-1 and *A. viridans*) to 57.14% (P4-4 and *M. hydrocarbonoclasticus*) (Table 10).

A value of DNA-DNA hybridization above 70% indicates the two organisms are the same species. P3-1 and P3-2 showed 100% and 72.06% hybridization, respectively, with *A. viridans* indicating that they are the same species. This agrees with the 16S rRNA gene sequencing data and FAME data published previously (Bruno, 2003, MSc. Thesis, Grenada, St. George's University).

P4-4 and *M. hydrocarbonoclasticus* showed 57.14% hybridization indicating that they are not the same species and distantly related. This agrees with the 16S rRNA gene sequencing published previously (Bruno) that indicated that P4-4 and *M. hydrocarbonoclasticus* are not the same genus.

P4-4 and *P. immobilis* showed 80% hybridization, indicating that they are the same species. This does not agree with the 16S rRNA gene sequencing data that indicated that P4-4 and *P. immobilis* are not the same genus. To confirm these results, P4-4 will be sent for 16S rRNA gene sequencing using the entire gene instead of 500 bp and compared to the database.

The foregoing detailed description has been given for clearness of understanding only and no unnecessary limitations should be understood therefrom as modifications will be obvious to those skilled in the art.

While the invention has been described in connection with specific embodiments thereof, it will be understood that it is capable of further modifications and this application is intended to cover any variations, uses, or adaptations of the invention following, in general, the principles of the invention and including such departures from the present disclosure as come within known or customary practice within the art to which the invention pertains and as may be applied to the essential features hereinbefore set forth and as follows in the scope of the appended claims.

All publications cited herein are incorporated herein by reference for the purpose of disclosing and describing specific aspects of the invention for which the publication is cited.

TABLE 1

| Culture collection catalogue offish isolates | | | | | |
|---|---|---|---|---|---|
| Strain designation | Isolation source | Culture medium and incubation temperature | Gram stain | Antagonistic properties | Closest related species |
| P1-5 | Parrotfish | ASWA 29° C. | Gram + diplococci | Antibacterial | No match, *Desemzia incerta* |
| P2-2 | Parrotfish | ASWA 29° C. | Gram + cocci | Antibacterial | No match, *Desemzia incerta* |
| P3-1 | Parrotfish | ASWA 29° C. | Gram + diplococci | n.i. | *Aerococcus viridans* |
| P3-2 | Parrotfish | ASWA 29° C. | Gram + tetracocci | Antibacterial and possible anti-eukaryotic signaling molecule | *Aerococcus viridans* |
| P3-3 | Parrotfish | ASWA 29° C. | Gram + cocci, clumps | Antibacterial | n.d. |
| P4-4 | Parrotfish | ASWA 29° C. | Gram + coccobacilli | Antibacterial and possible anti-eukaryotic signaling molecule | No match, *Psychrobacter immobilis* |
| P5-1 | Parrotfish | ASWA 29° C. | Gram + bacilli chains | n.i. | n.d. |

TABLE 1-continued

Culture collection catalogue offish isolates

| Strain designation | Isolation source | Culture medium and incubation temperature | Gram stain | Antagonistic properties | Closest related species |
|---|---|---|---|---|---|
| P5-2 | Parrotfish | ASWA 29° C. | Gram + cocci | Possible anti-biofilm signaling molecule | *Staphylococcus warneri* |
| P5-3 | Parrotfish | ASWA 29° C. | Gram − cocci | Antibacterial | n.d. |
| P6-1 | Parrotfish | ASWA 29° C. | Gram + bacilli | n.i. | n.d. |
| P6-2 | Parrotfish | ASWA 29° C. | Gram + bacilli | n.i. | n.d. |
| P6-3 | Parrotfish | ASWA 29° C. | Gram + bacilli | Antibacterial | n.d. |
| P6-4 | Parrotfish | ASWA 29° C. | Gram + cocci | Antibacterial | n.d. |
| P6-5 | Parrotfish | ASWA 29° C. | Gram − bacilli | Antibacterial | n.d. |
| P6-6 | Parrotfish | ASWA 29° C. | Gram − bacilli | Antibacterial | n.d. |
| S1-1 | Red Snapper | ASWA 29° C. | Gram − cocci, chains | Antibacterial | n.d. |
| S1-3 | Red Snapper | ASWA 29° C. | Gram + cocci | Antibacterial | n.d. |
| S2-1 | Red Snapper | ASWA 29° C. | Gram + diplococci | Antibacterial | n.d. |
| S2-2 | Red Snapper | ASWA 29° C. | Gram − bacilli | n.i. | n.d. |
| S3-2 | Red Snapper | ASWA 29° C. | Gram + diplococci | Antibacterial | n.d. | n.i. = no inhibition;
n.d. = no data

TABLE 2

Morphology of the fish skin isolates

|  | Strain | Colony Pigment | Cell Morphology | Cell size (μm) |
|---|---|---|---|---|
| 1 | P1-5 | Transparent | Gram + diplococci | 1-2 |
| 2 | P2-2 | Transparent | Gram + cocci | 1-2 |
| 3 | P3-1 | Transparent | Gram + diplococci | 1-2 |
| 4 | P3-2 | White | Gram + tetracocci | 2-3 |
| 5 | P3-3 | Peach/White | Gram + cocci, clumps | 2-3 |
| 6 | P4-4 | Peach, spreads | Gram + coccobacilli | 1 × 3-5 |
| 7 | P5-1 | White/Peach | Gram + rods, chains | 1 × 2-3 |
| 8 | P5-2 | Orange | Gram + cocci | 1-3 |
| 9 | P5-3 | Orange/Peach | Gram − cocci | 1 |
| 10 | P6-1 | Transparent | Gram + rods | 1 × 3-5 |
| 11 | P6-2 | Transparent | Gram + rods | 1 × 3-5 |
| 12 | P6-3 | White small | Gram + rods | 2 × 5-7 |
| 13 | P6-4 | Peach | Gram + rods | 1-3 |
| 14 | P6-5 | Yellow opaque | Gram − rods | 1 × 3 |
| 15 | P6-6 | Yellow transp. | Gram − rods | 1 × 3 |
| 16 | S1-1 | Yellow | Gram − cocci, chains | 1 |
| 17 | S1-3 | Orange | Gram + cocci | 1-2 |
| 18 | S2-1 | White | Gram + diplococci | 1-2 |
| 19 | S2-2 | Transparent | Gram − rods | 1 × 3 |
| 20 | S3-2 | Yellow | Gram + diplococci | 1-2 |

TABLE 3

Physiological characteristics of the isolates from the skin offish.

|  | Strain | Medium ASWA T 37° C. Salinity 40 ppt | Nutrient Agar (Difco) 28° C. Salinity 8 ppt | Blood Agar (Difco) 28° C. Hemolysis | Bacto Mannitol Salt Agar 28° C. (Difco) Acid production G + cocci | Catalase Test | Oxidase Test |
|---|---|---|---|---|---|---|---|
| 1 | P4-4 | Growth | Growth | γ | n.d. | + | + |
| 2 | P5-2 | Growth | Growth | α | n.d. | + | + |
| 3 | P3-2 | Growth | Growth | α | Acid | + | − |
| 4 | S1-1 | Growth | Growth | α | n.d. | + | − |
| 5 | S1-3 | Growth | Growth | α | Growth | + | + |
| 6 | P3-3 | Growth | Growth | γ | No growth | − | + |
| 7 | P5-1 | Growth | Growth | No growth | n.d. | + | + |
| 8 | S2-1 | Growth | Growth | α | Growth | + | + |
| 9 | P5-3 | Growth | Growth | No growth | n.d. | + | + |
| 10 | P1-5 | Growth | Growth | α | Acid | − | − |
| 11 | P2-2 | Growth | Growth | α | Acid | − | − |
| 12 | P3-1 | Growth | Growth | γ | Acid | − | − |
| 13 | S3-2 | Growth | Growth | α | Growth | + | + |
| 14 | S2-2 | Growth | Growth | α | n.d. | + | − |
| 15 | P6-1 | No growth | No growth | β | n.d. | + | − |
| 16 | P6-2 | No growth | No growth | β | n.d. | + | + |
| 17 | P6-3 | No growth | No growth | No growth | n.d. | − | − |
| 18 | P6-4 | No growth | No growth | γ | Growth | − | + |
| 19 | P6-5 | Growth | Growth | γ | n.d. | + | − |
| 20 | P6-6 | No growth | No growth | α | n.d. | + | + |

+ = positive reaction
− = negative reaction
α = alpha hemolysis
β = beta hemolysis
γ = gamma hemolysis

TABLE 4

Summary of antagonistic activity of isolates against reference strains for the extract test and streak test that yielded positive results.

| Strain Designation | S. aureus | s. epidermidis | Micrococcus spp. | E. clocae | K. pneumonia | P. vulgaris |
|---|---|---|---|---|---|---|
| P4-4 | 0.5 | n.i. | 1.5 | n.i. | 0.5 | 1 |
| S1-1 | n.i. | 1 | 0.5 | n.i. | n.i. | 1.5 |
| P3-2 | n.i. | 1 | n.i. | n.i. | n.i. | n.i. |
| S1-3 | 0.5 | 1 | n.i. | n.i. | n.i. | n.i. |
| P3-3 | n.i. | n.i. | n.i. | n.i. | n.i. | n.i. |
| S2-1 | 0.5 | n.i. | n.i. | n.i. | n.i. | 1 |
| P5-3 | n.i. | n.i. | n.i. | n.i. | n.i. | 1.5 |
| P1-5 | n.i. | 2-3 | n.i. | n.i. | n.i. | n.i. |
| P1-5 | n.i. | n.i. | 0.5 | n.i. | n.i. | n.i. |
| P2-2 | 1 | 1-2.5 | n.i. | n.i. | n.i. | n.i. |
| P2-2 | n.i. | n.i. | 0.5 | 0.5 | n.i. | 1 |
| P3-1 | n.i. | 2 | n.i. | n.i. | n.i. | n.i. |
| P3-1 | 1.5 | n.i. | n.i. | n.i. | n.i. | 1 |
| S3-2 | n.i. | 1 | n.i. | n.i. | n.i. | 1 |
| P6-3 | n.i. | 1 | n.i. | n.i. | n.i. | n.i. |
| P6-4 | n.i. | n.i. | 0.5 | n.i. | n.i. | 1 |
| P6-5 | n.i. | n.i. | n.i. | n.i. | n.i. | 3 |
| P6-5 | n.i. | 3 | n.i. | n.i. | n.i. | n.i. |
| P6-6 | n.i. | 2 | n.i. | 0.5 | n.i. | 2 |
| P6-6 | 5 | 4 | n.i. | n.i. | 1-5 | n.i. | n.i. = no inhibition mucus = extract isolated from mucus produced by the organism Zones of clearance for streak tests of active isolates (shaded) and extract tests of isolate extracts (not shaded) are in mm. The zones for the extract test are shown as the difference between test and control. Isolates that did not show inhibition are not shown.

TABLE 5

Summary of activity of living cells of isolates (P4-4, P5-2, P2-1, P3-2) against bacterial and eukaryotic fouling

| Strain | Inhibition of bacterial fouling | Inhibition of photosynthetic eukaryotic organisms | Inhibition of non-Photosynthetic eukaryotic | Antibacterial inhibition of reference strains | Possible nature |
|---|---|---|---|---|---|
| P4-4 | 49.5% p = 0.38 | 78.2% p = 0.009 | 52.47% p = 0.18 | n.d. | Anti-photosynthetic eukaryotic signal |
| P5-2 | 32.3% p = 0.62 | 45.36% p = 0.155 | 40.57% p = 0.81 | n.i. | No significant activity |
| P3-2 | 68.9% p = 0.31 | 22.47% p = 0.143 | 35.14% p = 0.21 | 6 | Bacteriocidal |
| P2-1 | 0% | 0% | 39.86% p = 0.13 | n.i. | No significant activity | n.d. = no data
n.i. = no inhibition
p = p value associated with t-test
Values in bold are associated with significant P values from t-test.

Antibacterial results are represented as diameter of clearance zone in mm. Mean bacterial colony area was used to estimate inhibition of bacterial fouling and counts of eukaryotic cells were used to estimate inhibition of eukaryotic fouling.

TABLE 6

Summary of extract activity of isolates (P4-4, P5-2, P2-1, P3-2) against bacterial and eukaryotic fouling.

| Strain | Inhibition of bacterial fouling | Inhibition of photosynthetic eukaryotic organisms | Inhibition of non-photosynthetic eukaryotic organisms | Antibacterial inhibition of reference strains | Possible nature |
|---|---|---|---|---|---|
| P4-4 | 63.2% p = 0.099 | 36.5% p = 0.094 | 0% | 6.5-9.5 | Bacteriocidal |
| P5-2 | 84.5% p = 0.024 | .60% p = 0.982 | 35.7% p = 0.191 | n.d. | Anti-biofilm signal |
| P3-2 | 82.0% p = 0.061 | 41.7% p = 0.013 | 39.86% p = 0.13 | n.i. | Anti-eukaryotic signal |

TABLE 6-continued

Summary of extract activity of isolates (P4-4, P5-2, P2-1, P3-2) against bacterial and eukaryotic fouling.

| Strain | Inhibition of bacterial fouling | Inhibition of photosynthetic eukaryotic organisms | Inhibition of non-photosynthetic eukaryotic organisms | Antibacterial inhibition of reference strains | Possible nature |
|---|---|---|---|---|---|
| P2-1 | 50.2% p = 0.185 | 8.8% p = 0.701 | 0% | n.d. | No significant activity | n.d. = no data
n.i. = no inhibition
p = p value associated with t-test
Values in bold are associated with significant P values from t-test.

Antibacterial results are represented as diameter of clearance zone in mm. Mean bacterial colony area was used to estimate inhibition of bacterial fouling and counts of eukaryotic cells were used to estimate inhibition of eukaryotic fouling.

TABLE 7

Taxonomic affiliation of the isolates.

| Strain designation | Similarity index from FA analyses | % difference of 500 bp in the 16S rRNA | Closest match or closest relative |
|---|---|---|---|
| p 3-2 | 0.554 | 0.28% | Aerococcus viridans |
| p 4-4 | n.d. | 5.15% | No match, Psychrobacter immobilis |
| p 5-2 | n.d. | 0.00% | Staphylococcus warneri |
| p 1-5 | 0.386 | n.d | No match, Desemzia incerta |
| p 2-2 | 0.367 | n.d. | No match, Desemzia incerta |
| p 3-1 | 0.523 | n.d. | Aerococcus viridans | n.d. = no data

TABLE 8

GC content for isolates P4-4, P3-2, P3-1, and P5-2 and closest related species.

| Organism | Purity of DNA (A250/A2ao) | % (G + C)* |
|---|---|---|
| P4-4 a | 1.65 | 40.77* |
| P4-4 b | 1.82 | 43.31* |
| P. immobilis a | 1.78 | 44.00 (to 47) |
| P. immobilis b | 2.04 | 44.00 (to 47) |
| M. hydrocarbonclasticus | 2.00 | n.d. |
| P3-1 | 1.55 | 43.99* |
| P3-2 | 1.65 | 41.67* |
| A. viridans | 1.49 | 35.00 (to 40) |
| P5-2 | 2.13 | 22.62* |
| S. warneri | 0.97 | 36.00 |

*= indicates adjusted %(G + C)
bold = indicates data from literature
n.d. = no data

TABLE 9

DNA-DNA hybridization for isolates P4-4, P3-2, P3-1, and P5-2 and closest related species.

| Organism | Adjusted % hybridized |
|---|---|
| P4-4 and P. immobilis | 80.00 |
| P4-4 and M. hydrocarbonclasticus | 57.14 |

TABLE 9-continued

DNA-DNA hybridization for isolates P4-4, P3-2, P3-1, and P5-2 and closest related species.

| Organism | Adjusted % hybridized |
|---|---|
| P3-1 and A. viridans | 100.00 |
| P3-2 and A. viridans | 72.06 |
| P5-2 and S. warneri | n.d. | n.d. = no data

The invention claimed is:

1. A composition comprising a culture medium for growing one or more bacteria identified as PTA-6763, PTA-6682, PTA-6764, PTA-6681 PTA-6765, or PTA-6766, wherein the culture medium comprises one or more bacteria identified as PTA-6763, PTA-6682, PTA-6764, and PTA-6681, and wherein the medium comprises one or more of agar, artificial sea water (ASW) medium, tryptic soy broth (TSB), brain heart infusion (BHI) broth, nutrient broth, and marine broth.

2. The composition of claim 1, wherein the culture medium is conditioned culture medium for growing one or more of the bacteria identified as PTA-6763, PTA-6682, PTA-6764, PTA-6681, PTA-6765, or PTA-6766.

3. The composition of claim 2, wherein the composition comprises supernatant of the culture medium for growing one or more of the bacteria identified as PTA-6763, PTA-6682, PTA-6764, PTA-6681, PTA-6765, or PTA-6766.

4. The composition of claim 3, wherein the composition comprises an extract of the supernatant of the culture medium for growing one or more of the bacteria identified as PTA-6763, PTA-6682, PTA-6764, PTA-6681, PTA-6765, or PTA-6766.

5. A paint or a coating comprising the composition of claim 2.

6. A method of protecting a surface from fouling, wherein the method comprises painting or coating the surface with the paint or coating of claim 5.

7. A polymeric matrix comprising the composition of claim 2.

8. A medical device or industrial equipment comprising the polymeric matrix of claim 7.

9. A paint or a coating comprising the composition of claim 3.

10. A method of protecting a surface from fouling, wherein the method comprises painting or coating the surface with the paint or coating of claim 9.

11. A polymeric matrix comprising the composition of claim 3.

12. A medical device or industrial equipment comprising the polymeric matrix of claim 11.

13. The composition of claim 1, wherein the agar comprises one or more of nutrient agar, blood agar, mannitol salts agar, artificial sea water agar (ASWA), brain heart infusion (BHI) agar, marine agar, and trypticase soy agar.

14. The composition of claim 1, wherein the culture medium comprises one or more bacteria grown to stationary phase.

15. The composition of claim 1, wherein the culture medium comprises one or more bacteria grown for 48 hours.

16. A paint or a coating comprising the composition of claim 4.

17. A method of protecting a surface from fouling, wherein the method comprises painting or coating the surface with the paint or coating of claim 16.

18. A polymeric matrix comprising the composition of claim 4.

19. A medical device or industrial equipment comprising the polymeric matrix of claim 18.

20. A method of inhibiting formation of biofilm on a surface or inhibiting the growth of microorganisms or a method of killing microorganisms, wherein the method comprises contacting the surface with the composition of claim 2.

21. The method of claim 20, wherein the surface comprises the surface of a medical device or the surface of an industrial system.

22. The method of claim 21, wherein the surface is an inert surface, a metallic surface, or a surface comprising polymeric materials.

23. The method of claim 20, wherein the surface is an inert surface or a surface of a living or dead organism.

24. The method of claim 23, wherein the surface of the living or dead organism is the surface of a human or animal tissue.

25. A method of inhibiting formation of biofilm on a surface or inhibiting the growth of microorganisms or a method of killing microorganisms, wherein the method comprises contacting the surface with the composition of claim 3.

26. A method of inhibiting formation of biofilm on a surface or inhibiting the growth of microorganisms or a method of killing microorganisms, wherein the method comprises contacting the surface with the composition of claim 4.

* * * * *